(12) United States Patent
Zhang et al.

(10) Patent No.: US 11,584,762 B1
(45) Date of Patent: Feb. 21, 2023

(54) NEAR-INFRARED FLUORESCENT INDICATORS FOR LYSOSOME AND APPLICATION THEREOF

(71) Applicant: DALIAN UNIVERSITY OF TECHNOLOGY, Dalian (CN)

(72) Inventors: Xinfu Zhang, Dalian (CN); Yi Xiao, Dalian (CN); Xiangli Li, Dalian (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 0 days.

(21) Appl. No.: 17/873,248

(22) Filed: Jul. 26, 2022

(51) Int. Cl.
| | |
|---|---|
| *C07F 5/02* | (2006.01) |
| *C09K 11/06* | (2006.01) |
| *G01N 21/64* | (2006.01) |
| *C09B 57/00* | (2006.01) |
| *C07D 517/14* | (2006.01) |
| *C07D 209/58* | (2006.01) |

(52) U.S. Cl.
CPC .......... *C07D 517/14* (2013.01); *C07D 209/58* (2013.01); *C07F 5/022* (2013.01); *C09B 57/00* (2013.01); *C09K 11/06* (2013.01); *G01N 21/64* (2013.01)

(58) Field of Classification Search
CPC ...................................................... C07F 5/022
See application file for complete search history.

(56) References Cited

FOREIGN PATENT DOCUMENTS

| | | |
|---|---|---|
| CN | 107098923 A | 8/2017 |
| CN | 110183482 A | 8/2019 |
| CN | 111961072 A | 11/2020 |

OTHER PUBLICATIONS

Kim et al. (European Journal of Organic Chemistry (2015), 25, 5563-5571).*
Title of the Item: "ACS Applied Materials & Interfaces" Publication date: Nov. 10, 2014 Name of the Author: Xinfu Zhang et al. Article Title:"A Photostable Near-Infrared Fluorescent Tracker with PH-Independent Specificity to Lysosomes for Long Time and Multicolor Imaging".
Title of the Item: "The Royal Society of Chemistry" Publication date: Aug. 28, 2019 Name of the Author: Xiangduo Kong et al. Article Title:"Lysosome-targeting tutn-on red/NIR BODIPY probes for imaging hypoxic cells".

* cited by examiner

*Primary Examiner* — Susanna Moore
(74) *Attorney, Agent, or Firm* — Nitin Kaushik

(57) ABSTRACT

The present disclosure relates to Near-infrared fluorescent indicators for lysosomes and application thereof. These indicators are composed of lipophilic NIR BODIPY derivatives and ionizable bis-tertiary amine moiety, which enable the formation of a transient amphiphilic state in acidic environments specifically. This structural feature affords accurate lysosomal membrane targeting ability at nanomole staining concentration.

3 Claims, 7 Drawing Sheets

NEAR-INFRARED FLUORESCENT INDICATORS FOR LYSOSOME AND APPLICATION THEREOF

CROSS-REFERENCE TO RELATED APPLICATIONS

The application claims priority to Chinese patent application No. 202110848756.1, filed on Jul. 27, 2021, the entire contents of which are incorporated herein by reference.

TECHNICAL FIELD

The present disclosure relates to Near-infrared fluorescent indicators for lysosomes and application thereof, and belongs to the field of fine chemicals.

BACKGROUND

Lysosomes play a critical role in various physiological activities, such as metabolism, cell apoptosis, and circulation of cellular membrane. Lysosomes are highly dynamic and can constantly change their morphology and spatial distribution. Visually tracking lysosomes and detecting their active species, specific microenvironment and key physiological process helps to disclose the molecular mechanism of life activities. In order to implement the above functions, fluorescent probes with excellent photophysical properties, good lysosome specificity and weak interference to the physiological functions of lysosomes are needed. In recent years, many fluorescent indicators targeting lysosomes have been reported, most of which are within the visible light range (400-650 nm). These indicators are not in favor of multicolor imaging due to overlap with autofluorescence or other indicators. Fluorescent indicators in the NIR region show the advantages of deep imaging level in tissue sample, long imaging window for multicolor imaging with other indicators, and weak photo-toxicity.

Therefore, what is needed are fluorescent indicators for lysosomes in the near-infrared region that show stable targeting performance and ultra-bright emission. The compounds disclosed herein address these and other needs.

SUMMARY

The present disclosure provides a class of near-infrared fluorescent indicators for lysosomes based on BODIPY and application thereof. These indicators are amphiphilic, in acidic environment can target lysosomes in low concentration and stay in lysosomes stably for quite a long time. These indicators have the following structure formula:

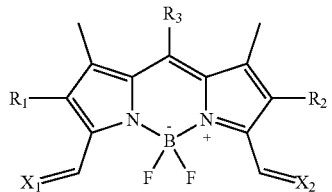

Where, R1, R2 are each independently H, Cl, Br or I;
R3 is H, CH3, CF3, C3H6COOCH3, C2H4COOC2H5, C2H5, X1 is 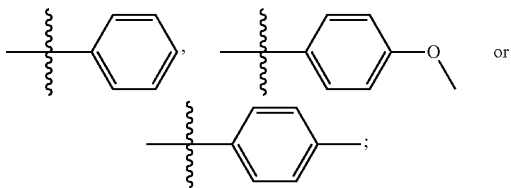

X2 is H or 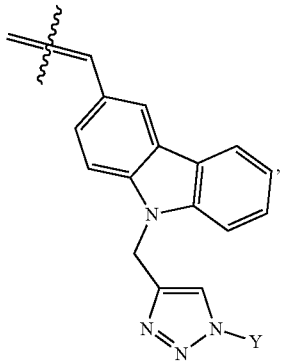

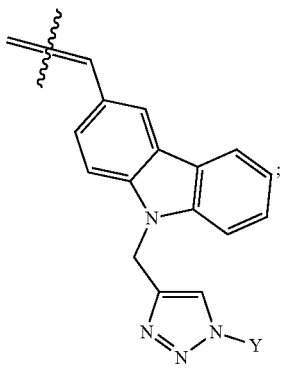

Y is each independently

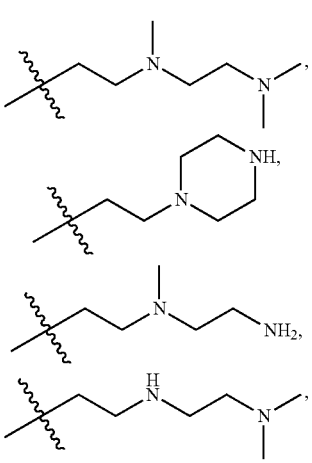

-continued

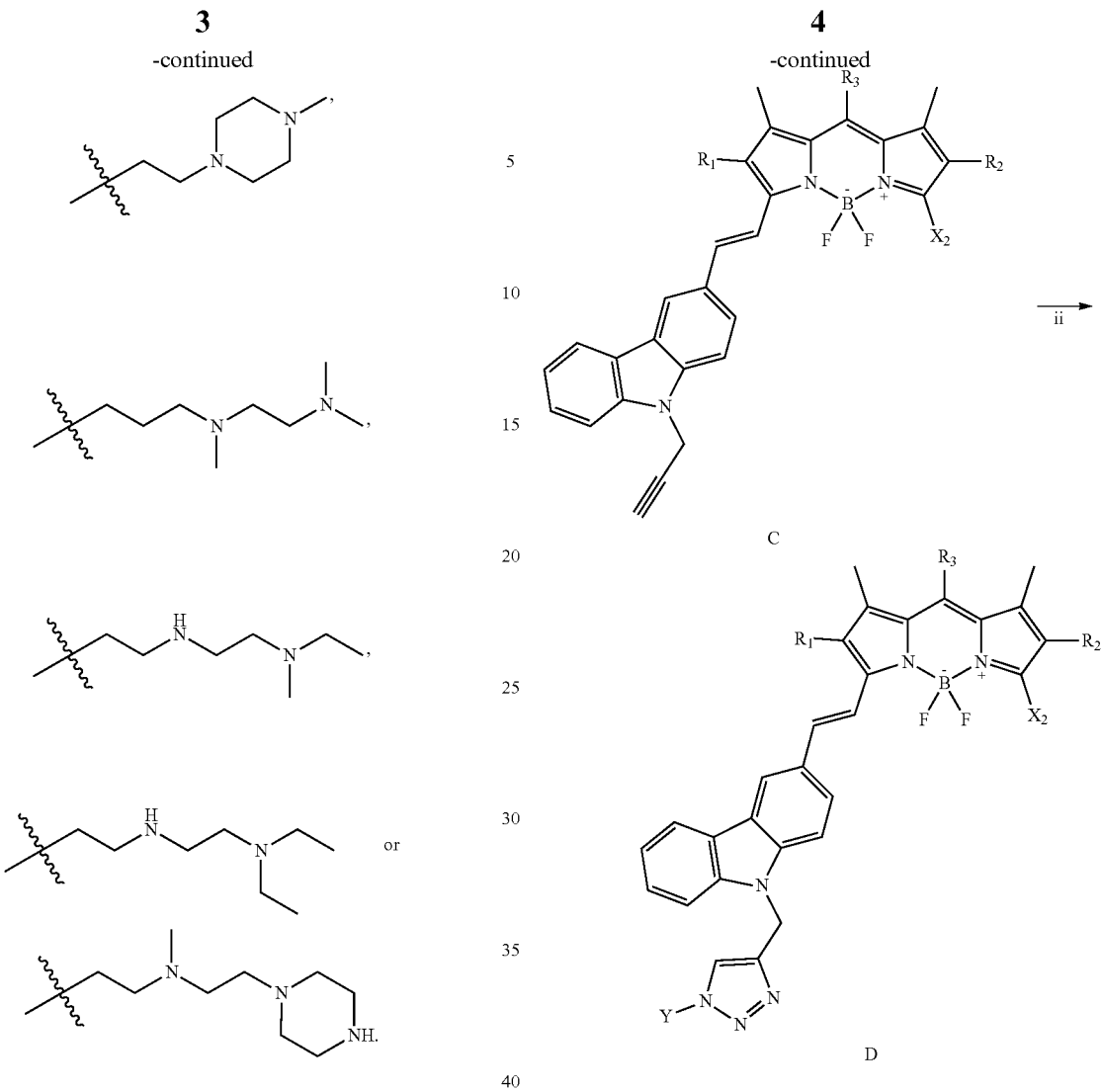

Provided herein is the method for preparing these indicators, which includes the following reacting formula and steps:

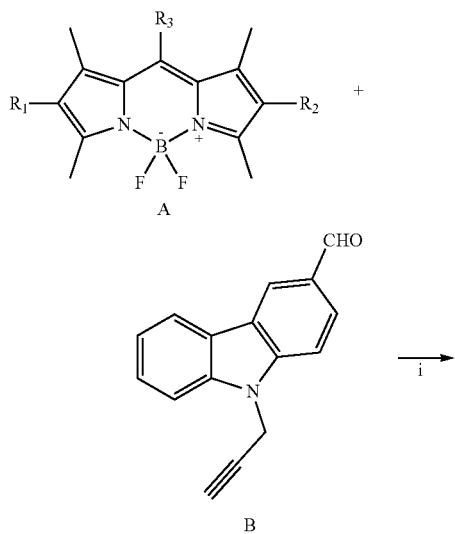

i) A mixture of compounds A, B, piperidine, and glacial acetic acid are heated and stirred in organic solvents, using a water separator to remove water. The resulting mixture are concentrated, extracted with $CH_2Cl_2$, and then washed with brine. The combined organic phase is concentrated, dried, and purified by column chromatography to obtain compound C.

ii) Under argon protection, compound Y-N3 are added to organic solvents, copper sulfate dissolved in water and sodium ascorbate are added. Compound C is dissolved in organic solvent and dropped into the above reacting solution, stirred at room temperature. Then the resulting mixture are concentrated, extracted with $CH_2Cl_2$, and then washed with brine. The combined organic phase is concentrated, dried, and purified by column chromatography to obtain compound D.

Wherein, the definition of R1, R2, R3, X and Y are the same as in the structure of formula.

In step i, the organic solvent is one or more selected from the group consisting of benzene, toluene, xylene, chlorobenzene, dichlorobenzene, dioxane, nitrogen methyl pyrrolidone, dimethylformamide, dimethyl acetamide, dimethyl sulfoxide, hexamethyl phosphoramide, sulfolane, and benzonitrile, the reacting temperature is between 90 and 150° C. In step ii, the reacting temperature is room temperature, the solvent is one selected from the group consisting of water, dimethylformamide, dimethyl acetamide, dimethyl sulfoxide, nitrogen methyl pyrrolidone, and acetonitrile.

Advantages of the present disclosure: these indicators described above introduced small hydrophilic (ionizable amino) groups onto the lipophilic BODIPY structure, excellent photophysical properties, including a high molar extinction coefficient (102,498-12,015 M1 cm-1), high quantum yield (up to 0.91), and tunable emission maximum ranging from 610 to 750 nm. High molar extinction coefficient and quantum yield afford ultra-brightness, which means they can work at very low concentrations and thus with low cytotoxicity. These indicators demonstrate typical aggregation-caused quenching (ACQ) effect in water, while good dispersion and fluorescence in CTAB micellar. This feature is highly in favor of imaging without washing, and therefore enhancing targeting accuracy and imaging quality.

The present invention provides a series of ultra-bright and stable fluorescent trackers of the lysosomal membrane for confocal and STED-based super-resolution imaging. These trackers are composed of lipophilic NIR BODIPY derivatives and ionizable bis-tertiary amine moiety, which enable the formation of a transient amphiphilic state in acidic environments specifically. This structural feature affords accurate lysosomal membrane targeting ability at nanomole staining concentration.

BRIEF DESCRIPTION OF DRAWINGS

The present application is described herein below with reference to the accompanying drawings, in which.

DETAILED DESCRIPTION OF THE EMBODIMENTS

Figure 1:
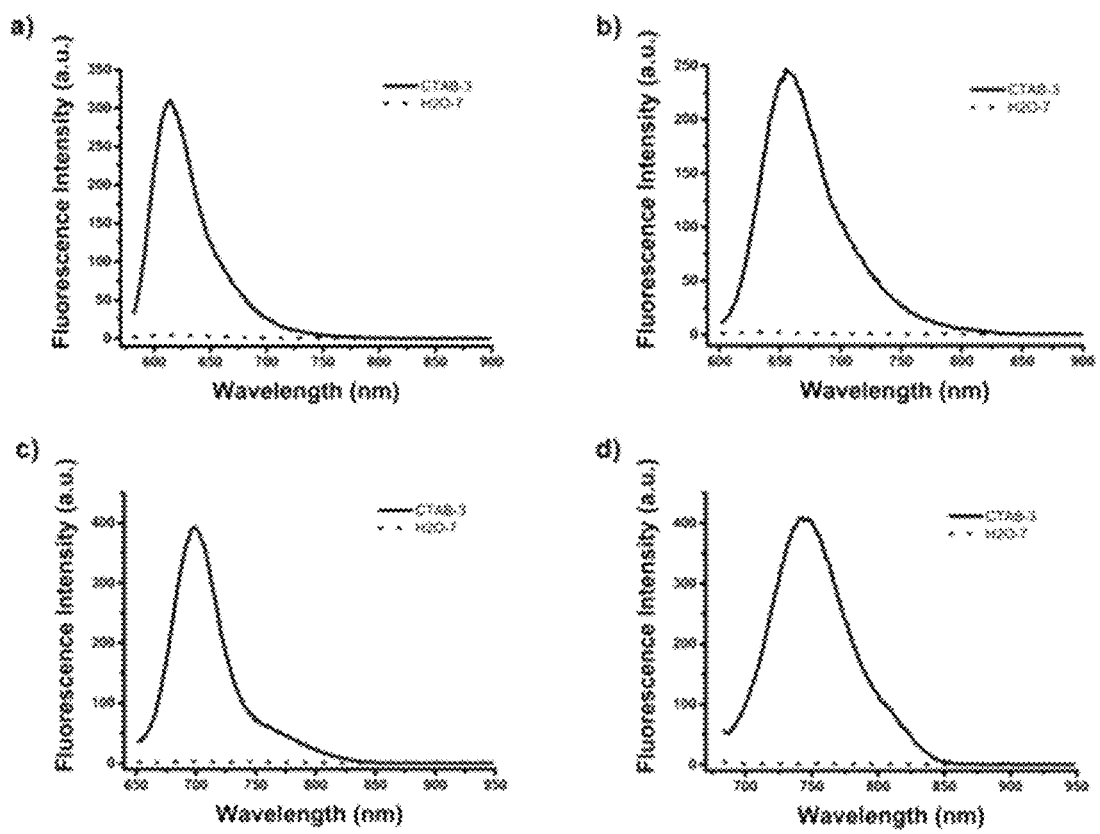
FIG. 1 is the emission spectrum of compounds D1, D2, D25 and D26 in different solvents.

In order to clarify the technical solutions of the present application, the examples of the present application will be described clearly and completely in conjunction with the technical solutions and the drawings. The following examples are intended to describe but not limit the present application.

Example 1

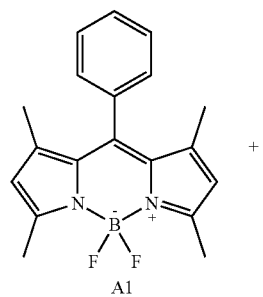

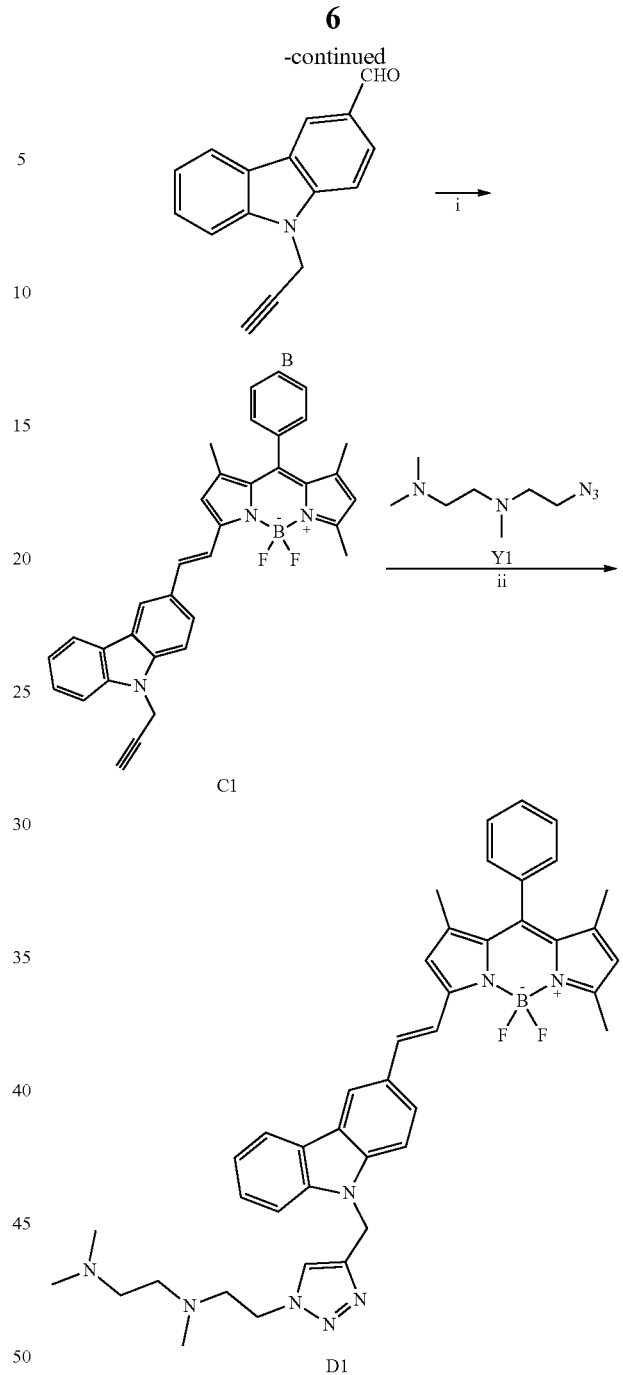

i) A1 (1.27 mmol) and B (1.27 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH$_2$Cl$_2$/Petroleum ether, 1/3) to obtain compound C1.

ii) Under argon protection, compound C11 (82 μmol), Y1 (164 μmol), CuSO$_4$.H$_2$O (82 μmol) and Na ascorbate (164

μmol) were added into the mixture solution consisting of toluene, ethanol, and water (v/v/v=12/4/1), the mixture was stirred at room temperature monitoring by TLC until compound C1 was consumed completely. The resulting mixture were concentrated and purified by column chromatography to obtain compound D1.

Example 2

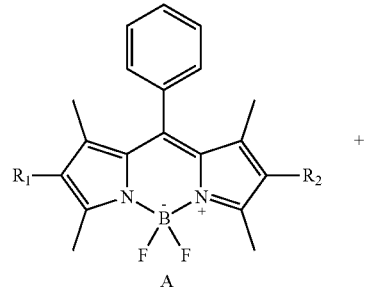

A

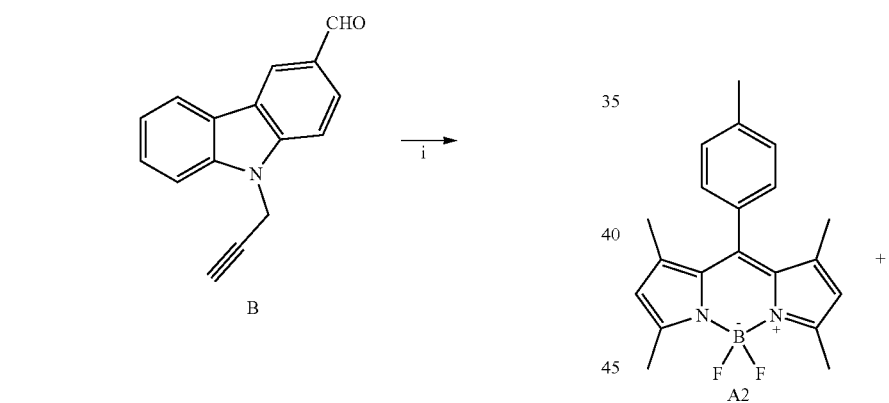

C

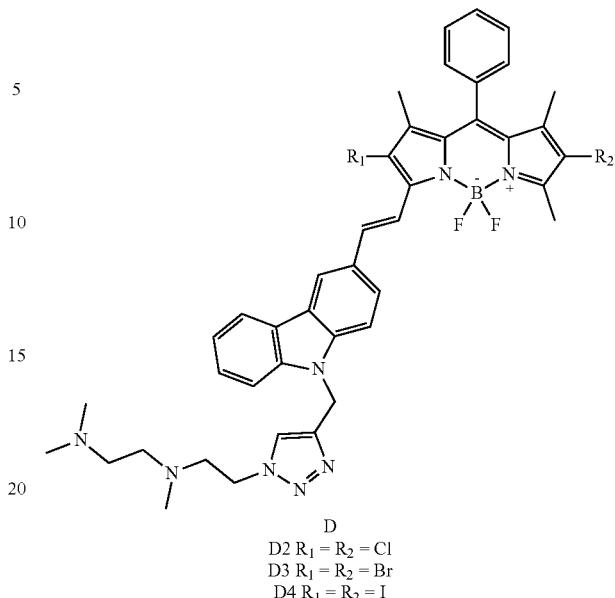

D
D2 R$_1$ = R$_2$ = Cl
D3 R$_1$ = R$_2$ = Br
D4 R$_1$ = R$_2$ = I

The synthesis method of compounds D2, D3 and D4 was the same as example 1.

Example 3

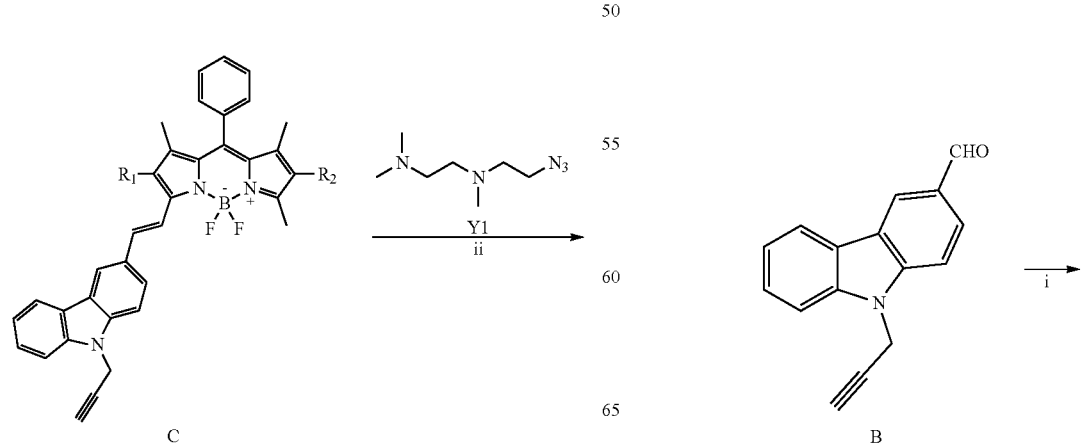

A2

B

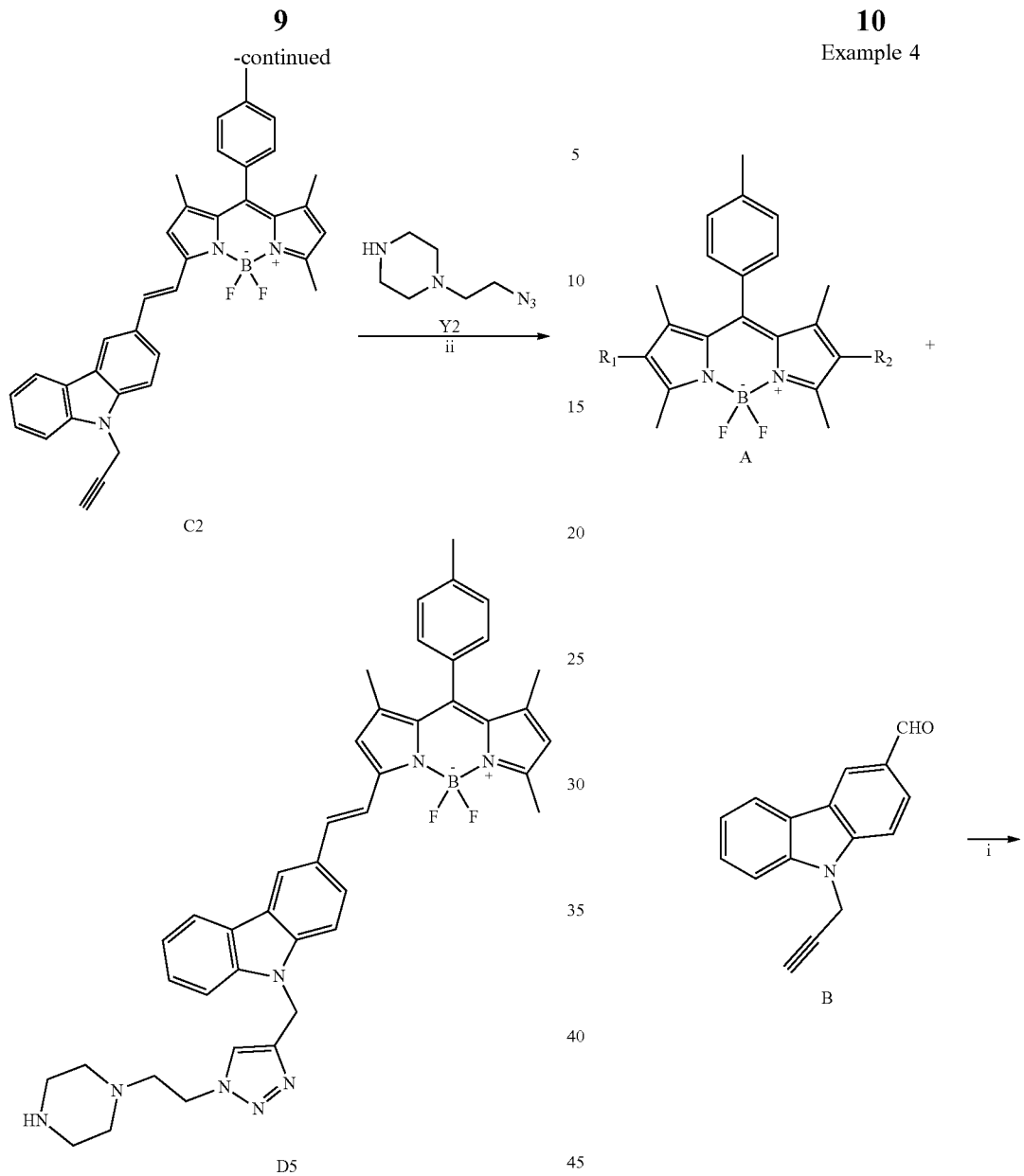

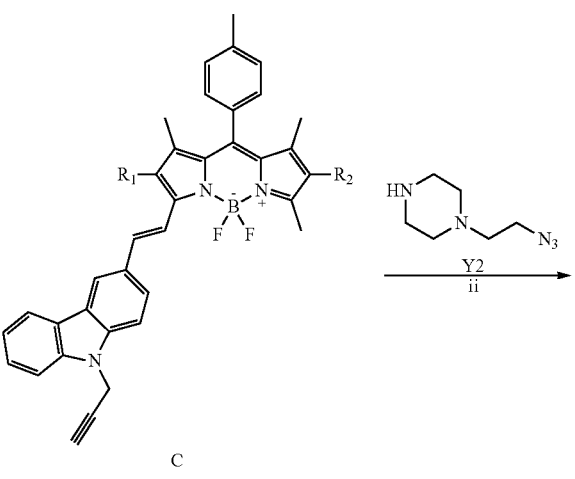

i) A2 (1.27 mmol), B (1.27 mmol) were added to 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH$_2$Cl$_2$/Petroleum ether, 1/3) to obtain compound C2.

ii) Under argon protection, compound C2 (82 μmol), Y2 (164 μmol), CuSO$_4$.H$_2$O (82 μmol) and Na ascorbate (164 μmol) were added into the mixture solution consisting of toluene, ethanol, and water (v/v/v=12/4/1), the mixture was stirred at room temperature monitoring by TLC until compound C2 was consumed completely. The resulting mixture was concentrated and purified by column chromatography to obtain compound D5.

11

-continued

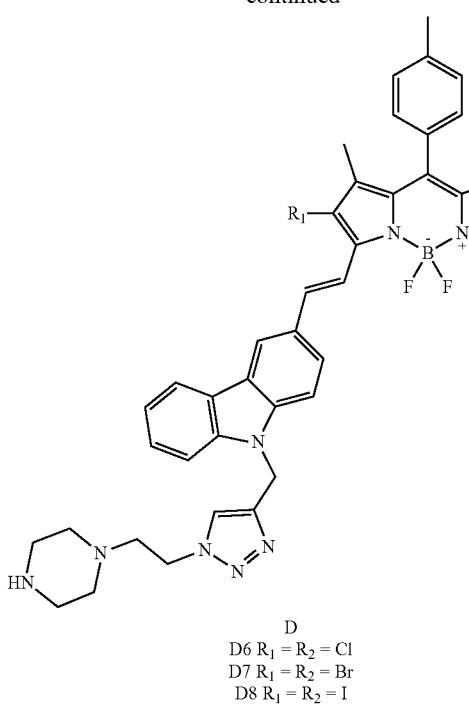

D
D6 R₁ = R₂ = Cl
D7 R₁ = R₂ = Br
D8 R₁ = R₂ = I

The synthesis method of compounds D6, D7 and D8 was the same as example 3.

Example 5

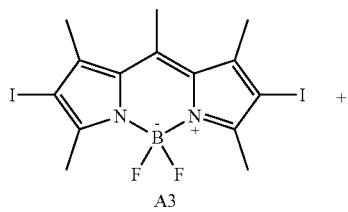

A3

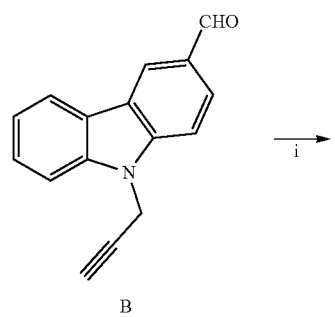

B

12

-continued

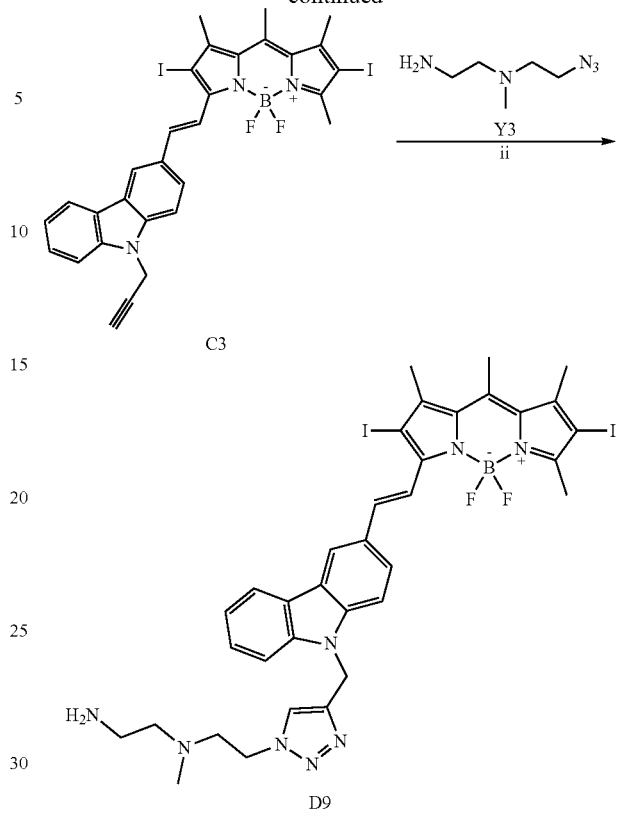

i) A3 (1.27 mmol) and B (1.27 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH₂Cl₂/Petroleum ether, 1/3) to obtain compound C3.

ii) Under argon protection, compound C3 (82 μmol), Y3 (164 μmol), CuSO₄.H₂O (82 μmol) and Na ascorbate (164 μmol) were added into the mixture solution consisting of toluene, ethanol, and water (v/v/v=12/4/1), the mixture was stirred at room temperature monitoring by TLC until compound C3 was consumed completely. The resulting mixture was concentrated and purified by column chromatography to obtain compound D9.

Example 6

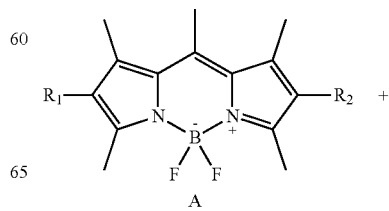

A

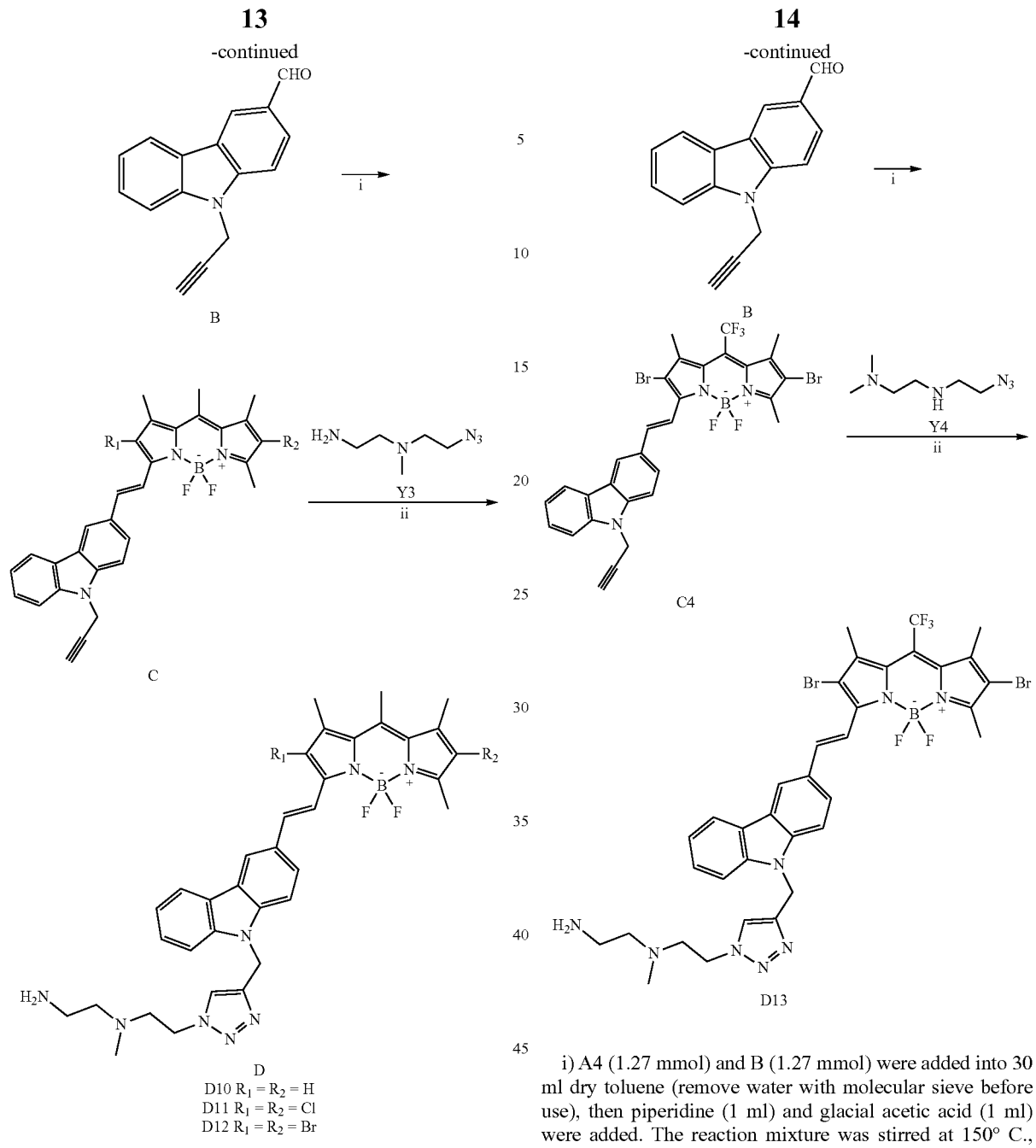

The synthesis method of compounds D10, D11 and D12 was the same as example 5.

Example 7

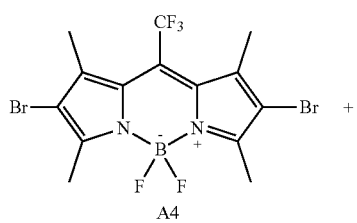

i) A4 (1.27 mmol) and B (1.27 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography ($CH_2Cl_2$/Petroleum ether, 1/3) to obtain compound C4.

ii) Under argon protection, compound C4 (82 μmol), Y4 (164 μmol), $CuSO_4·H_2O$ (82 μmol) and Na ascorbate (164 μmol) were added into the mixture solution consisting of toluene, ethanol, and water (v/v/v=12/4/1), the mixture was stirred at room temperature monitoring by TLC until compound C4 was consumed completely. The resulting mixture was concentrated and purified by column chromatography to obtain compound D13.

Example 8
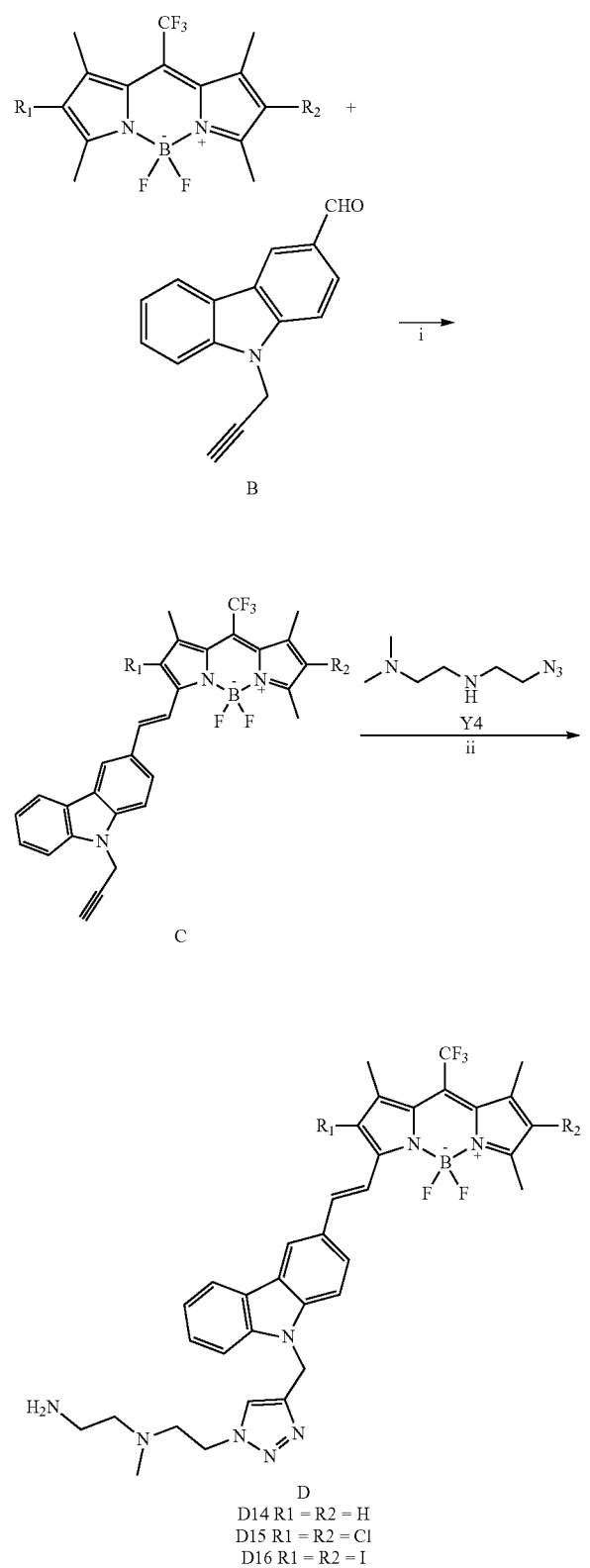
The synthesis method of compounds D14, D15 and D16 was the same as example 7.
Example 9
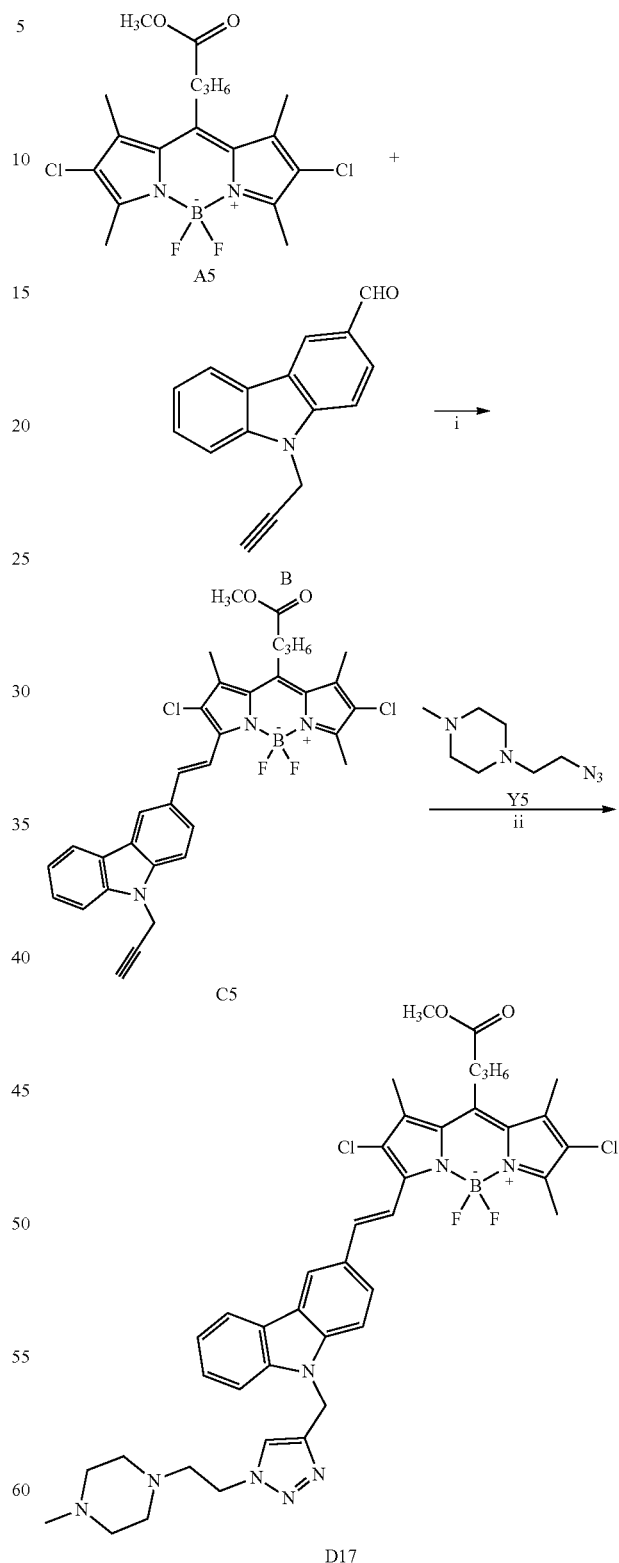
i) A5 (1.27 mmol) and B (1.27 mmol) were added into 30 ml dry toluene (remove water with molecular sieve before use), then piperidine (1 ml) and glacial acetic acid (1 ml)

were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH$_2$Cl$_2$/Petroleum ether, 1/3) to obtain compound C5.

ii) Under argon protection, compound C5 (82 μmol), Y5 (164 μmol), CuSO$_4$.H$_2$O (82 μmol) and Na ascorbate (164 μmol) were added into the mixture solution consisting of toluene, ethanol, and water (v/v/v=12/4/1), the mixture was stirred at room temperature monitoring by TLC until compound C5 was consumed completely. The resulting mixture was concentrated and purified by column chromatography to obtain compound D17.

Example 10

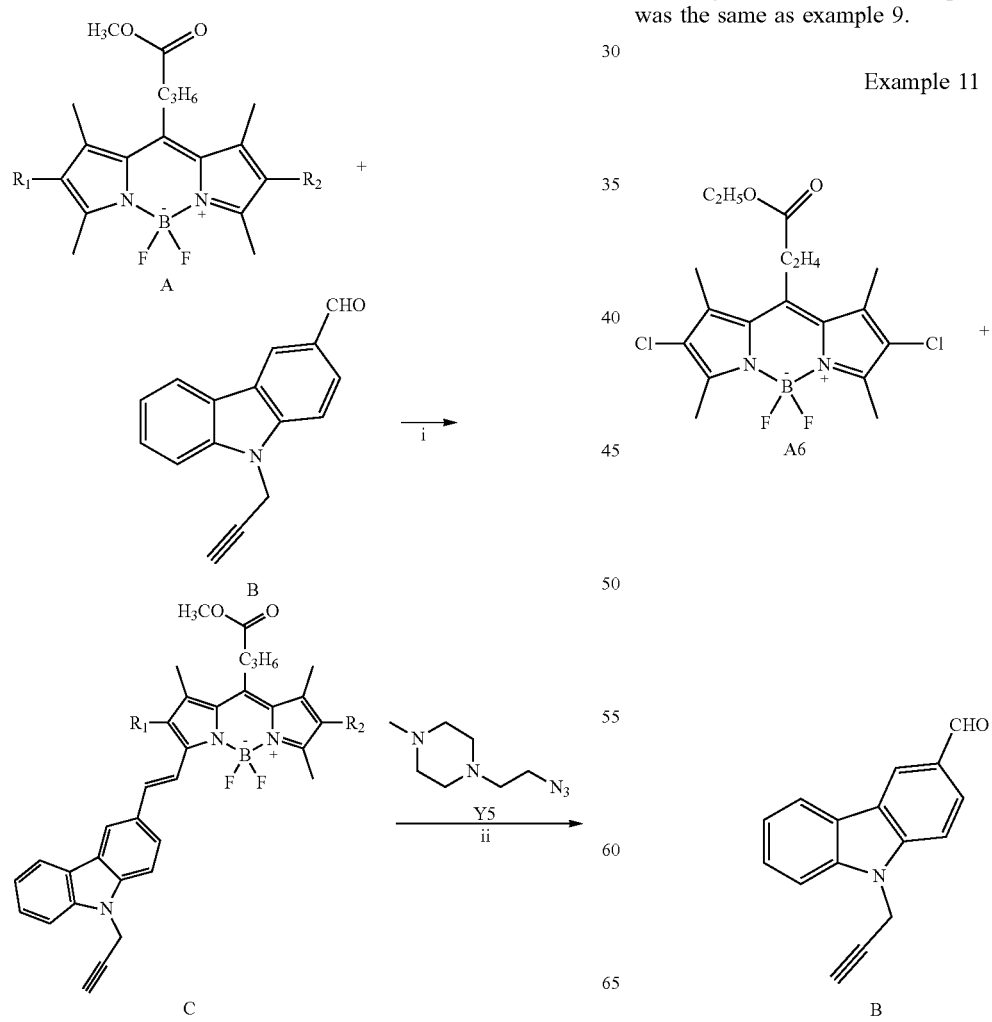

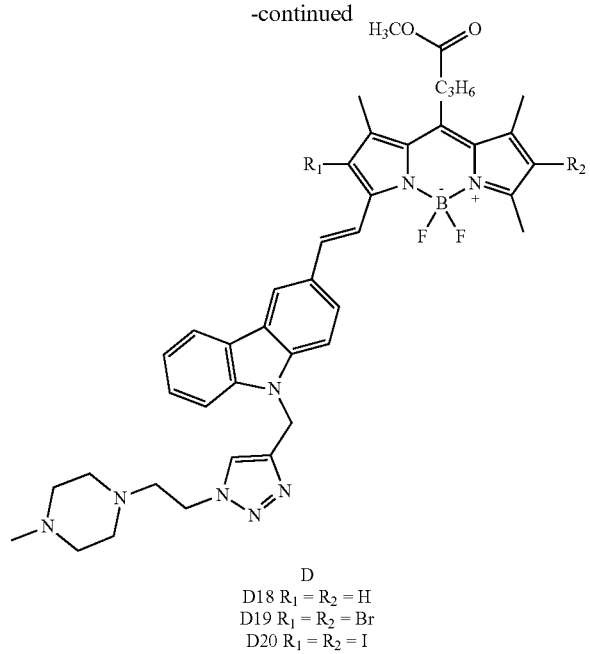

D
D18 R$_1$ = R$_2$ = H
D19 R$_1$ = R$_2$ = Br
D20 R$_1$ = R$_2$ = I

The synthesis method of compounds D18, D19 and D20 was the same as example 9.

Example 11

19

-continued

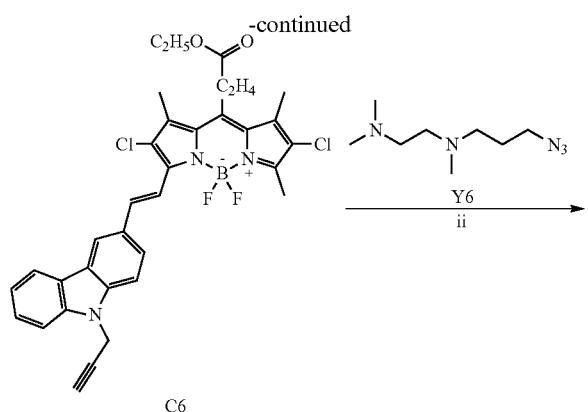

C6

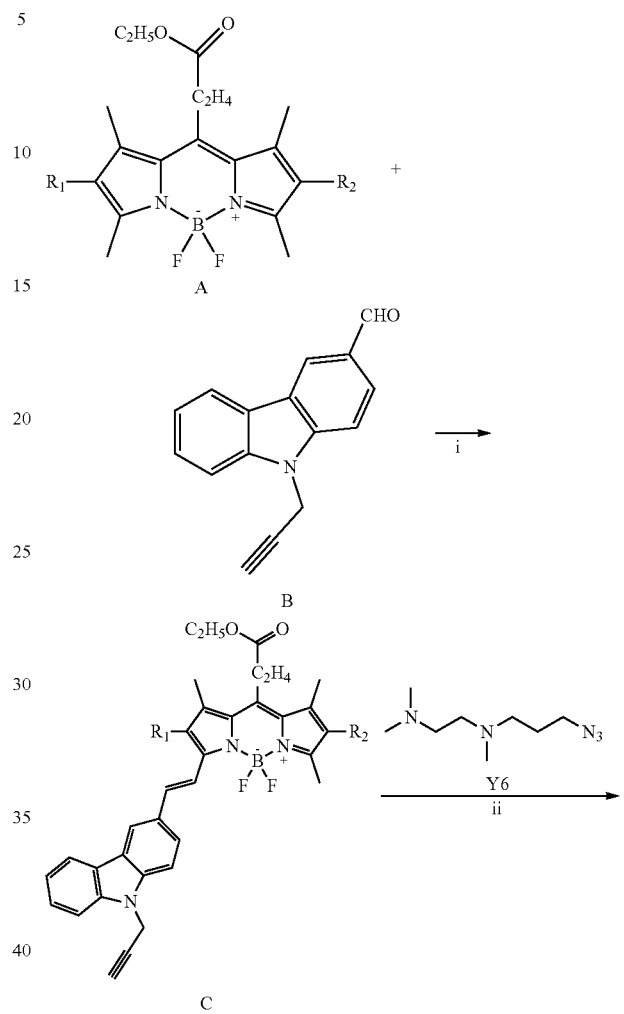

D21 i) A6 (1.27 mmol) and B (1.27 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH$_2$Cl$_2$/Petroleum ether, 1/3) to obtain compound C6.

ii) Under argon protection, compound C6 (82 μmol), Y6 (164 μmol), CuSO$_4$·H$_2$O (82 μmol) and Na ascorbate (164 μmol) were added into the mixture solution consisting of toluene, ethanol, and water (v/v/v=12/4/1), the mixture was stirred at room temperature monitoring by TLC until compound C6 was consumed completely. The resulting mixture was concentrated and purified by column chromatography to obtain compound D21.

20

Example 12

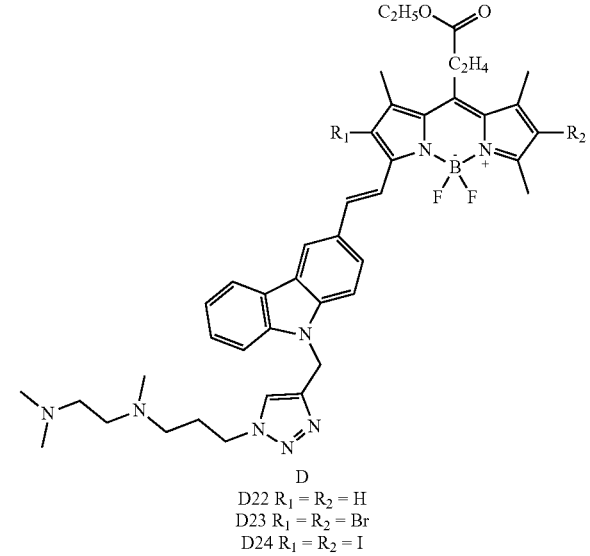

D
D22 R$_1$ = R$_2$ = H
D23 R$_1$ = R$_2$ = Br
D24 R$_1$ = R$_2$ = I

The synthesis method of compounds D22, D23 and D24 was the same as example 11.

Example 13
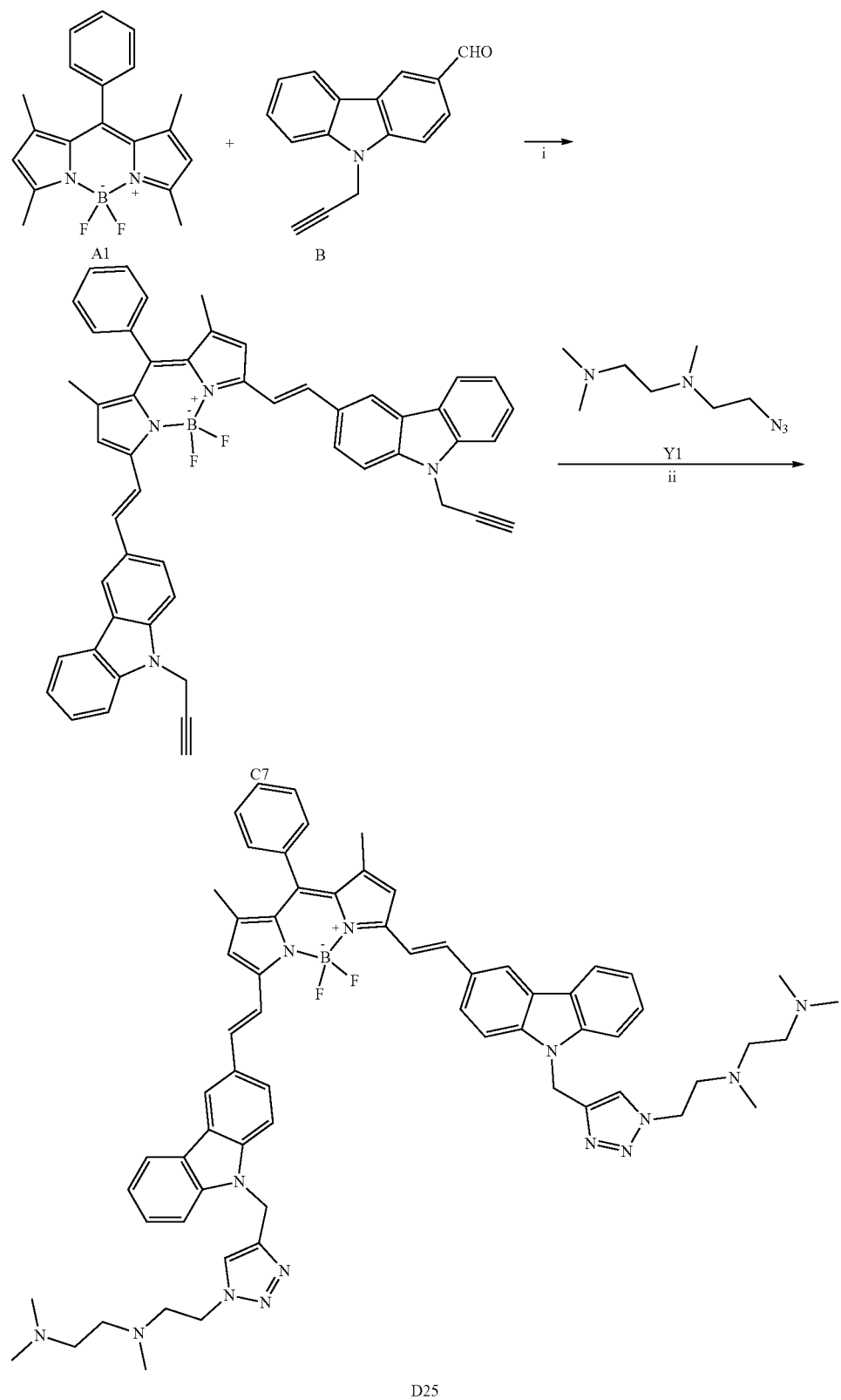
i) A1 (1.27 mmol) and B (3.81 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography ($CH_2Cl_2$/Petroleum ether, 1/3) to obtain compound C7.

ii) Under argon protection, compound C7 (66 μmol), Y1 (198 μmol), $CuSO_4 \cdot H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C7 was consumed completely. The resulting mixture was concentrated and purified by column chromatography to obtain compound D25.

Example 14

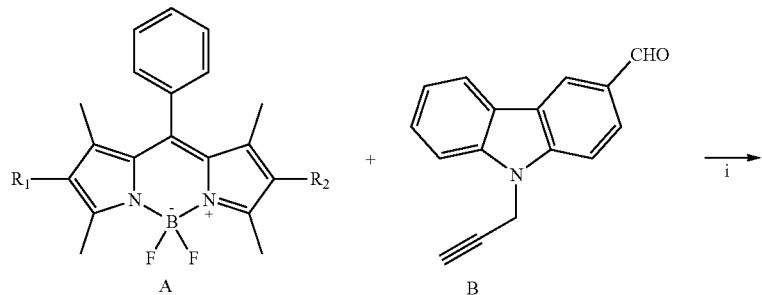

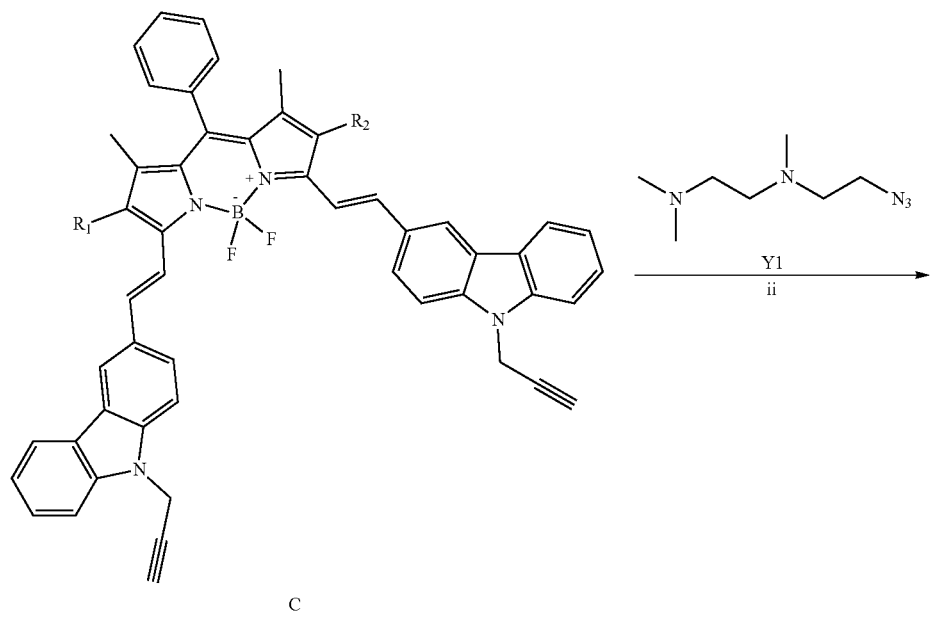

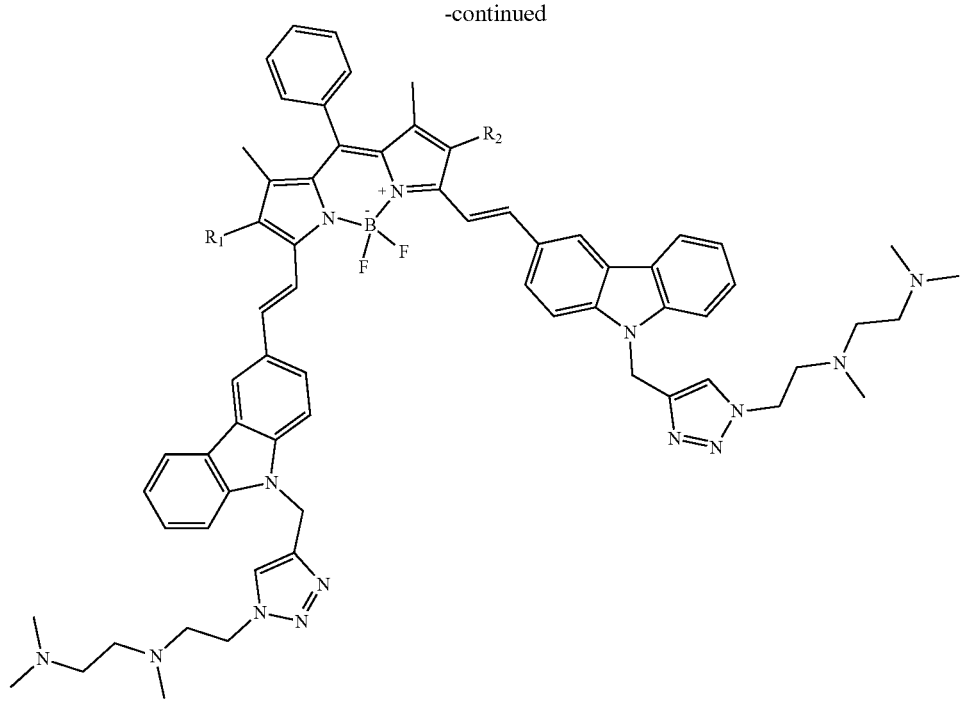
D
D26 R$_1$ = R$_2$ = Cl
D27 R$_1$ = R$_2$ = Br
D28 R$_1$ = R$_2$ = I
The synthesis method of compounds D26, D27 and D28 was the same as example 13.
Example 15
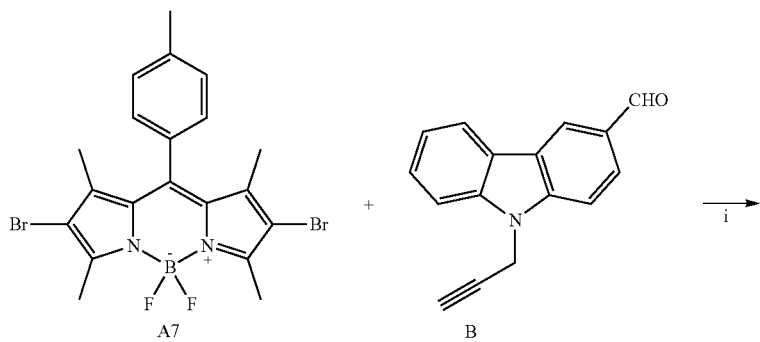

-continued

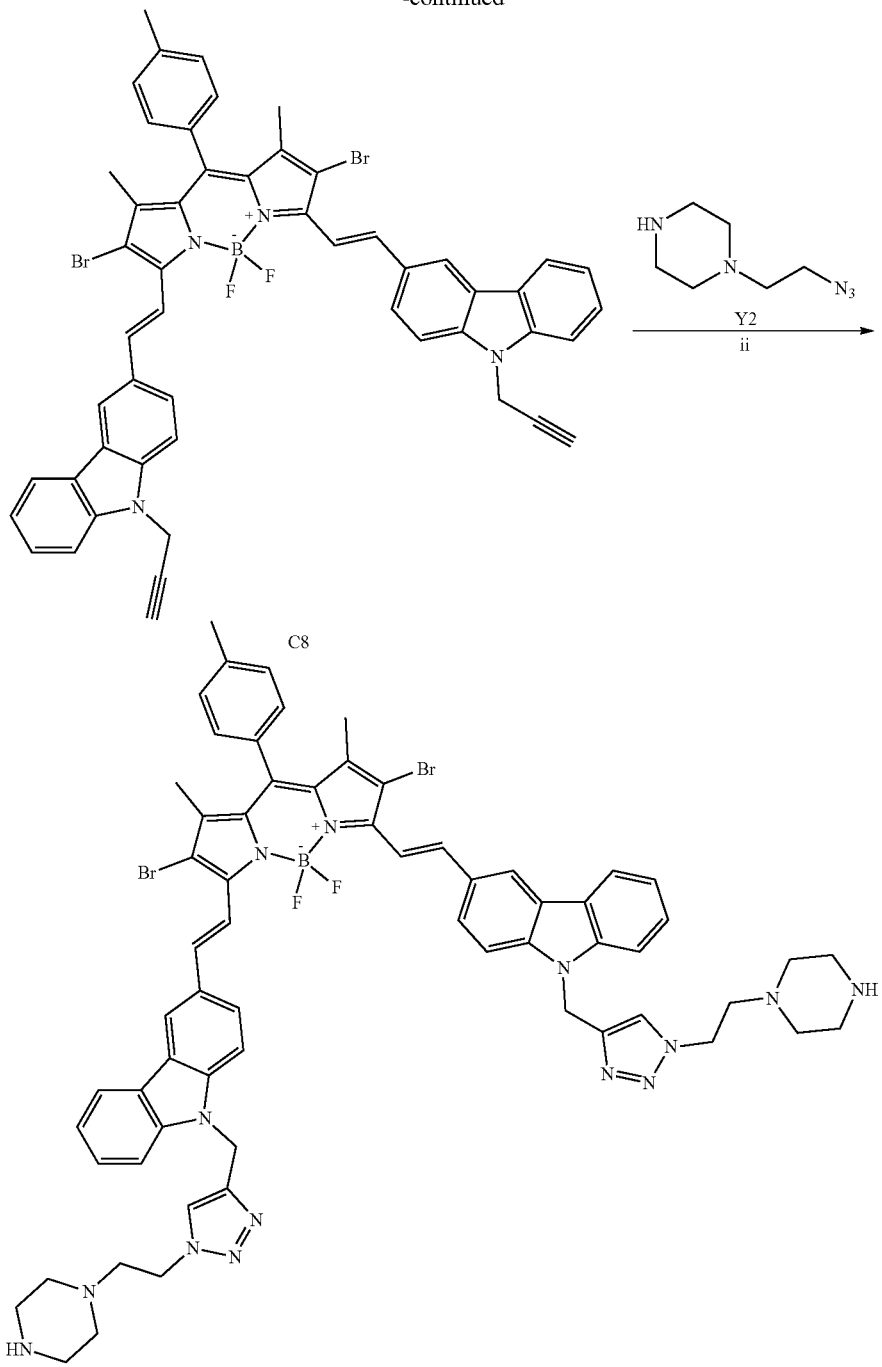

i) A7 (1.27 mmol) and B (3.81 mmol) were added into 30 ml dry toluene (remove water with molecular sieve before use) and stirred, piperidine (1 ml) and glacial acetic acid (1 ml) were added to, then the reaction mixture was stirred at 150° C., while the water produced during the reaction was removed by water separator. The reaction was monitored by TLC until the end of the reaction. After reducing to room temperature, most of the toluene in the reaction mixture was evaporated under vacuum, and the remaining mixture was diluted with dichloromethane, washed with water, and concentrated. The crude product was purified by column chromatography ($CH_2Cl_2$/Petroleum ether, 1/3) to obtain compound C8.

ii) Under argon protection, compound C8 (66 μmol), Y2 (198 μmol), $CuSO_4.H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C8 was consumed completely. The resulting mixture was concentrated and purified by column chromatography to obtain compound D29.

Example 16
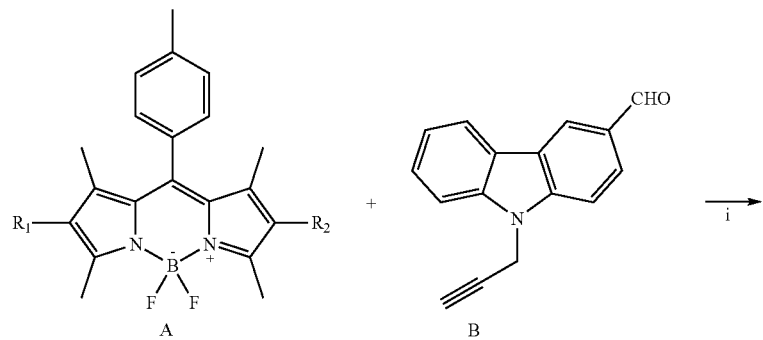
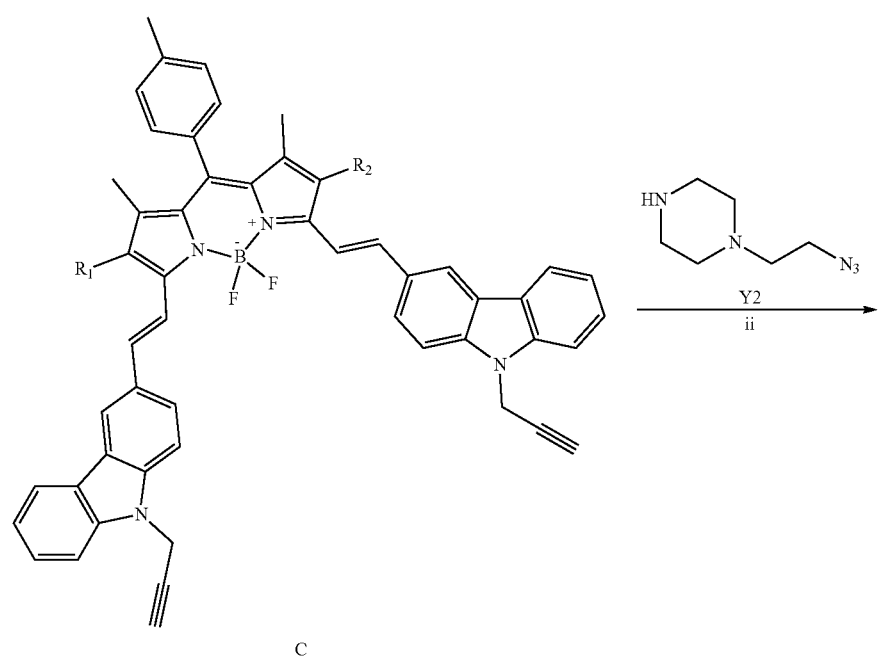

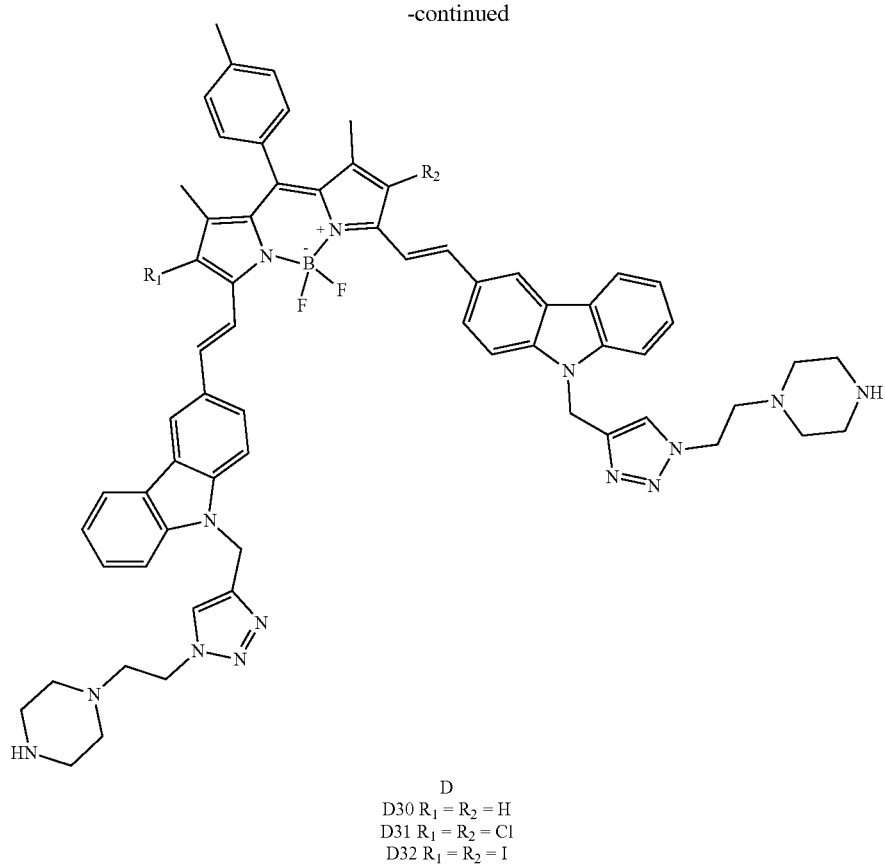
D
D30 R₁ = R₂ = H
D31 R₁ = R₂ = Cl
D32 R₁ = R₂ = I
The synthesis method of compounds D30, D31 and D32 was the same as example 15.
Example 17
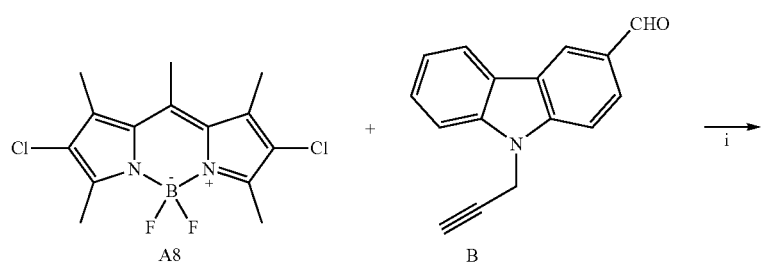

-continued

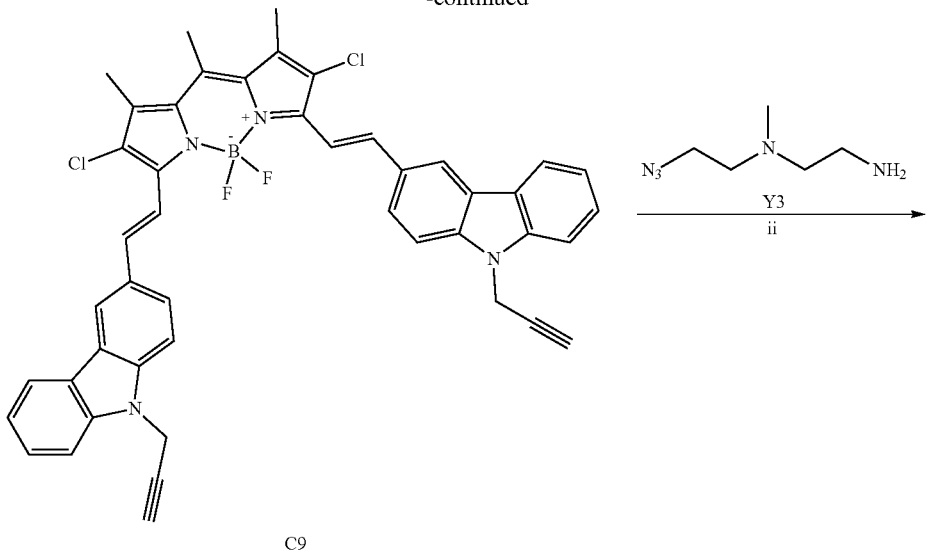

C9

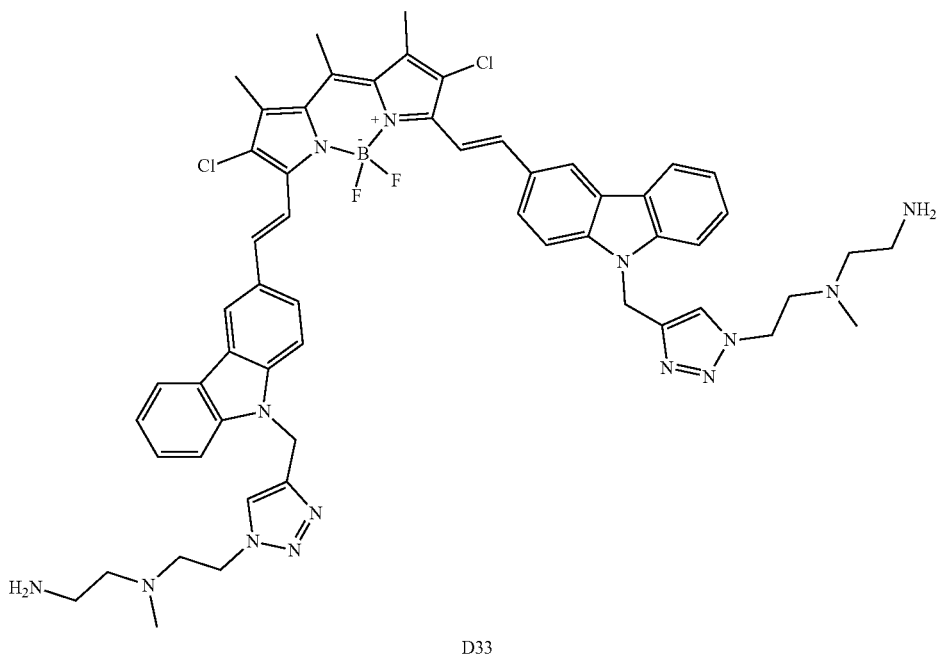

D33 i) A8 (1.27 mmol) and B (3.81 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography ($CH_2Cl2$/Petroleum ether, 1/3) to obtain compound C9.

ii) Under argon protection, compound C9 (66 μmol), Y3 (198 μmol), $CuSO_4.H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C9 was consumed completely. The resulting mixture was concentrated and purified by column chromatography to obtain compound D33.

Example 18
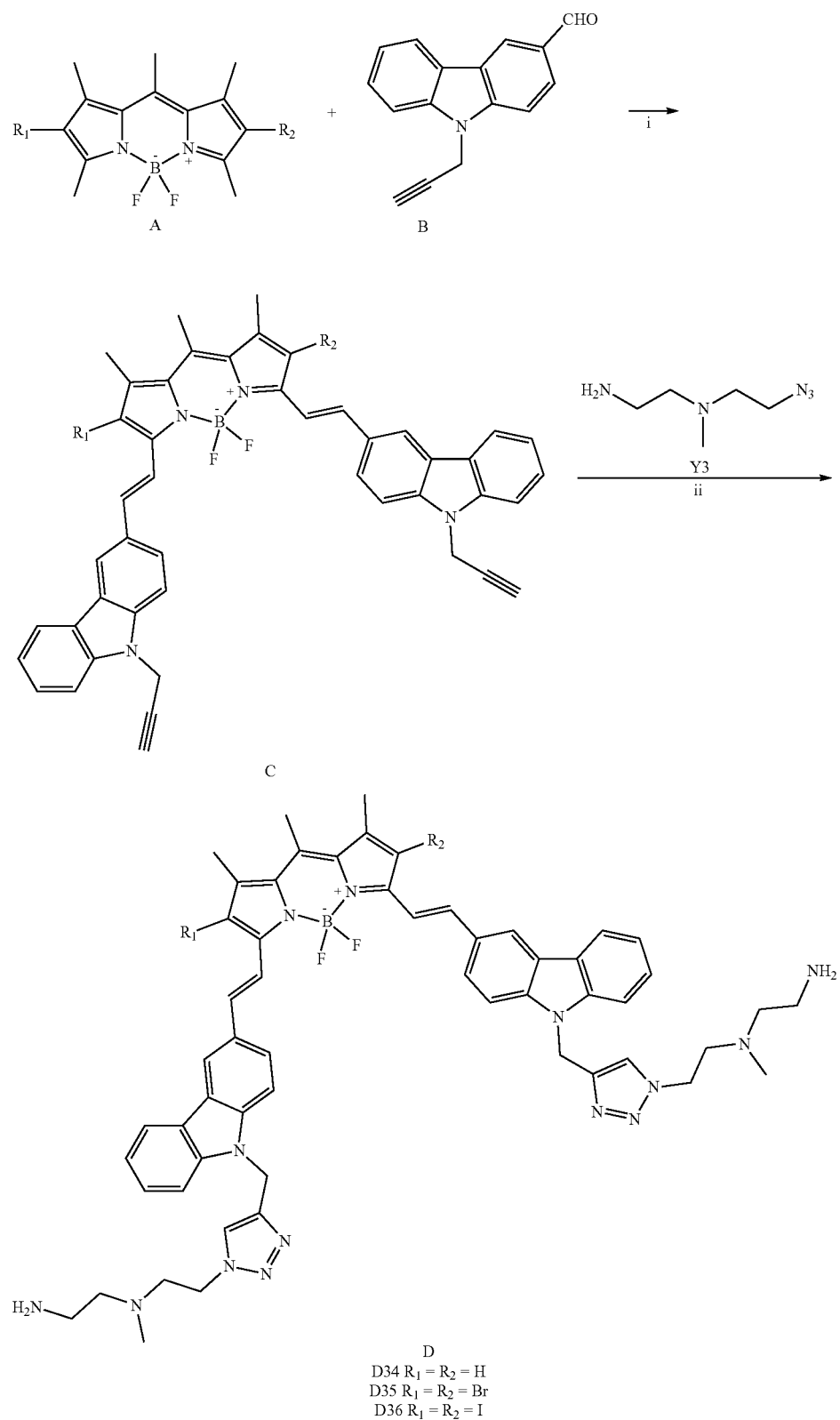
The synthesis method of compounds D34, D35 and D36 was the same as example 17.

Example 19

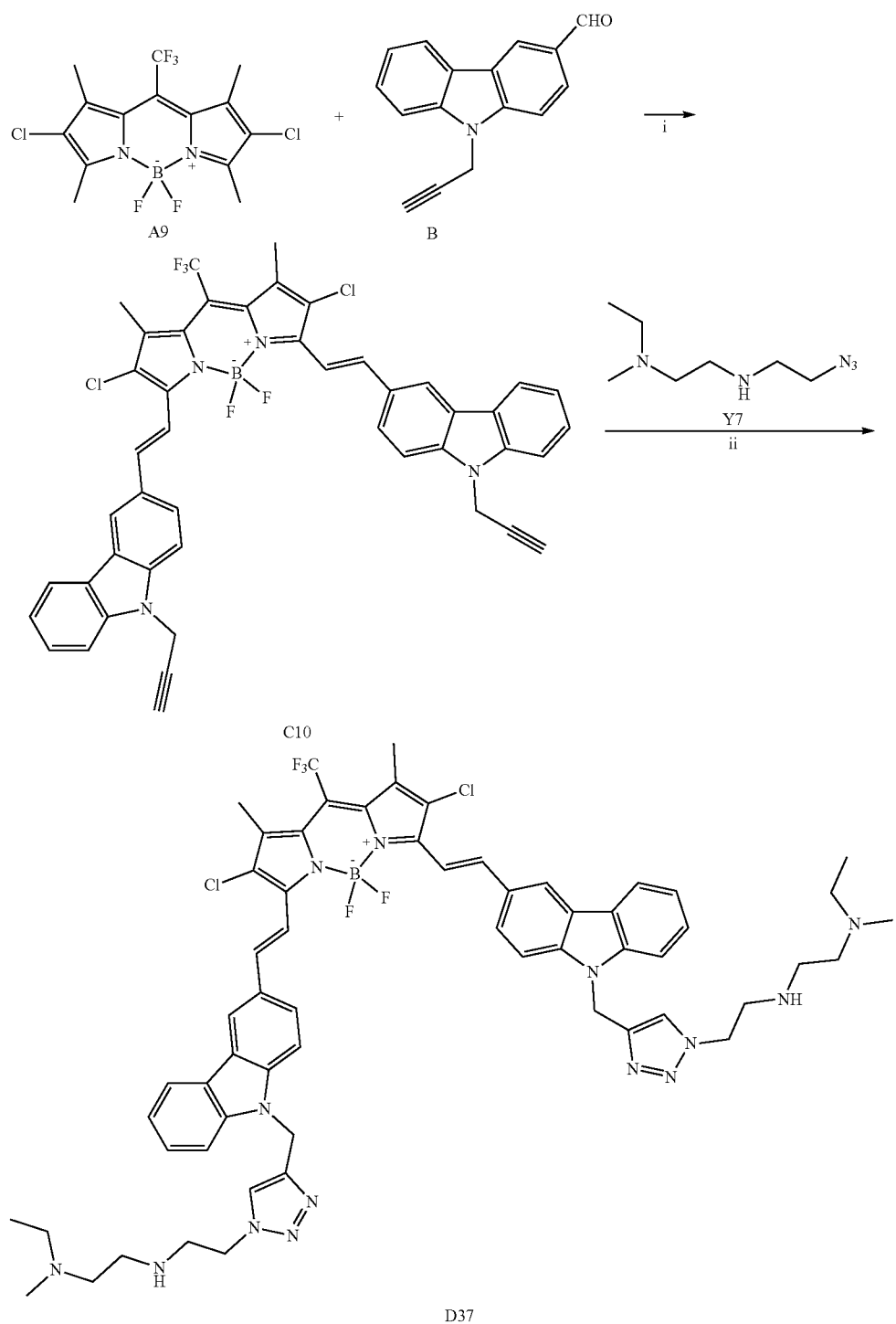

i) A9 (1.27 mmol) and B (3.81 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography ($CH_2Cl_2$/Petroleum ether, 1/3) to obtain compound C10.

ii) Under argon protection, compound C10 (66 μmol), Y7 (198 μmol), $CuSO_4 \cdot H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C10 was consumed completely. The resulting mixture was concentrated and purified by column chromatography to obtain compound D37.
Example 20
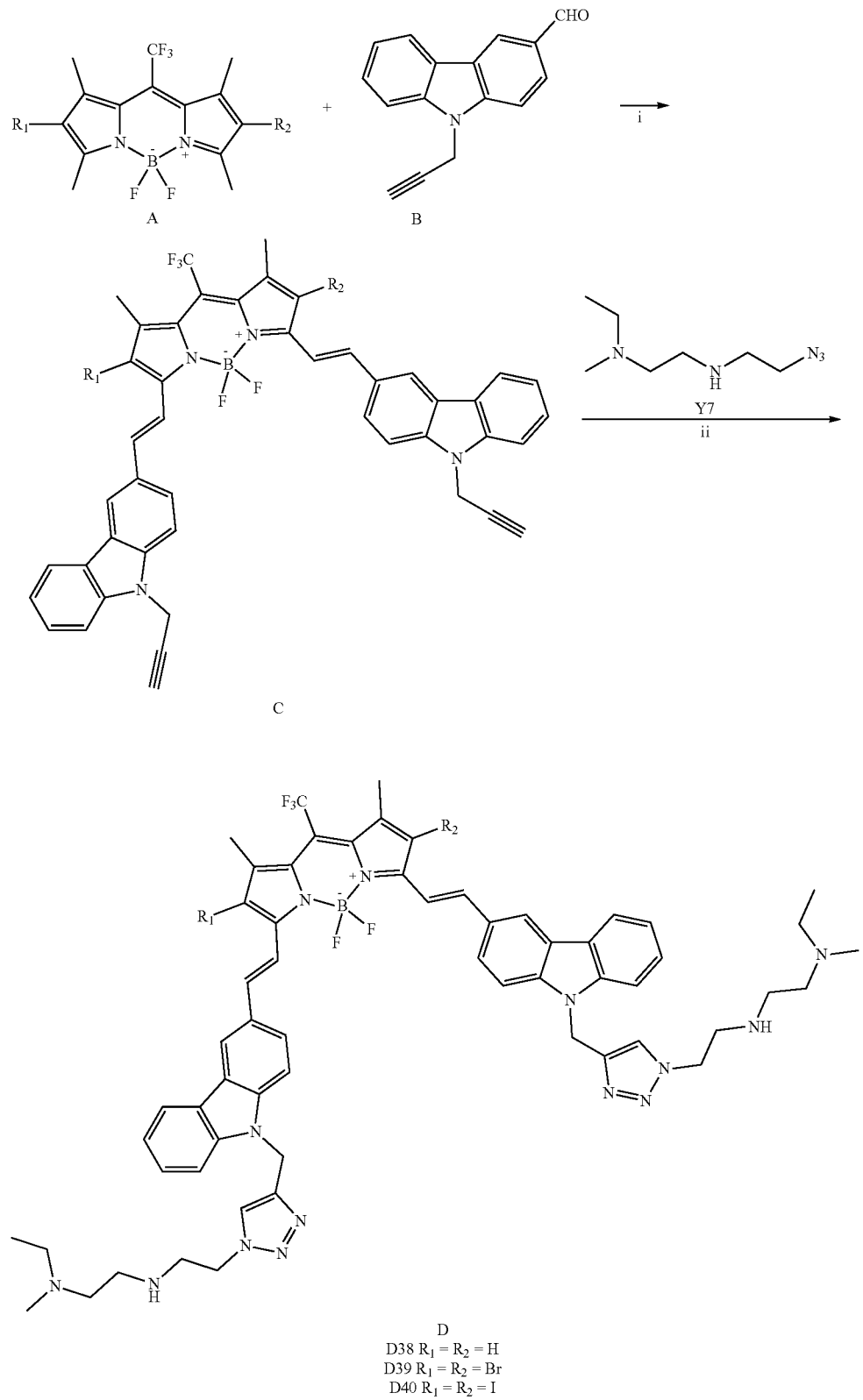

The synthesis method of compounds D38, D39 and D40 was the same as example 19.
Example 21
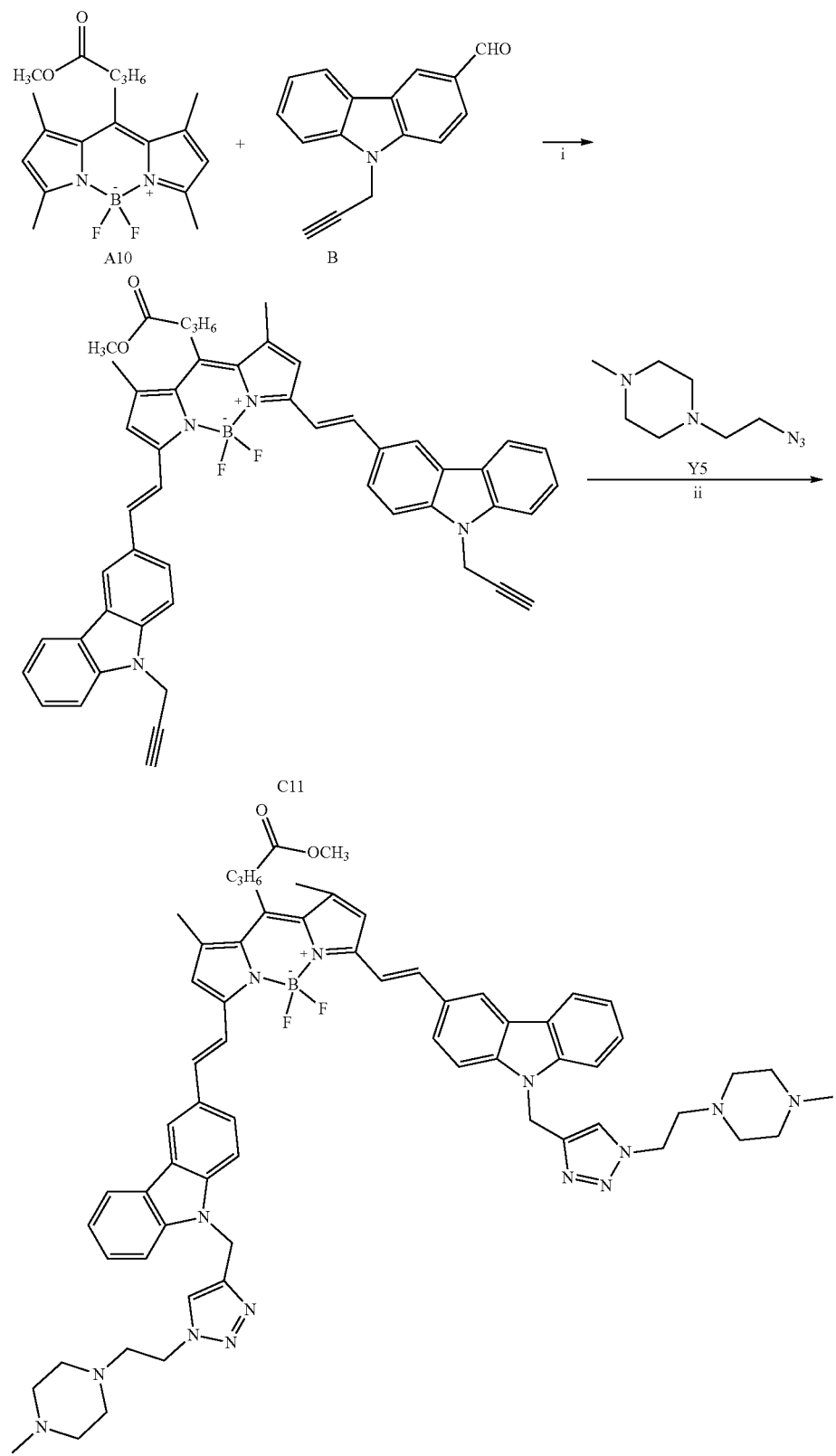

i) A10 (1.27 mmol) and B (3.81 mmol) were added into 30 ml dry toluene (remove water with molecular sieve before use), then piperidine (1 ml) and glacial acetic acid (1 ml) were added. The reaction mixture was stirred at 150° C., while the water produced during the reaction was removed by a water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography (CH$_2$Cl$_2$/Petroleum ether, 1/3) to obtain compound C11.

ii) Under argon protection, compound C11 (66 μmol), Y5 (198 μmol), CuSO$_4$.H$_2$O (66 μmol) and Na ascorbate (132 μmol) were added into the mixture solution consisting of toluene, ethanol, and water (v/v/v=12/4/1), the mixture was stirred at room temperature monitoring by TLC until compound C11 was consumed completely. The resulting mixture was concentrated and purified by column chromatography to obtain compound D41.

Example 22

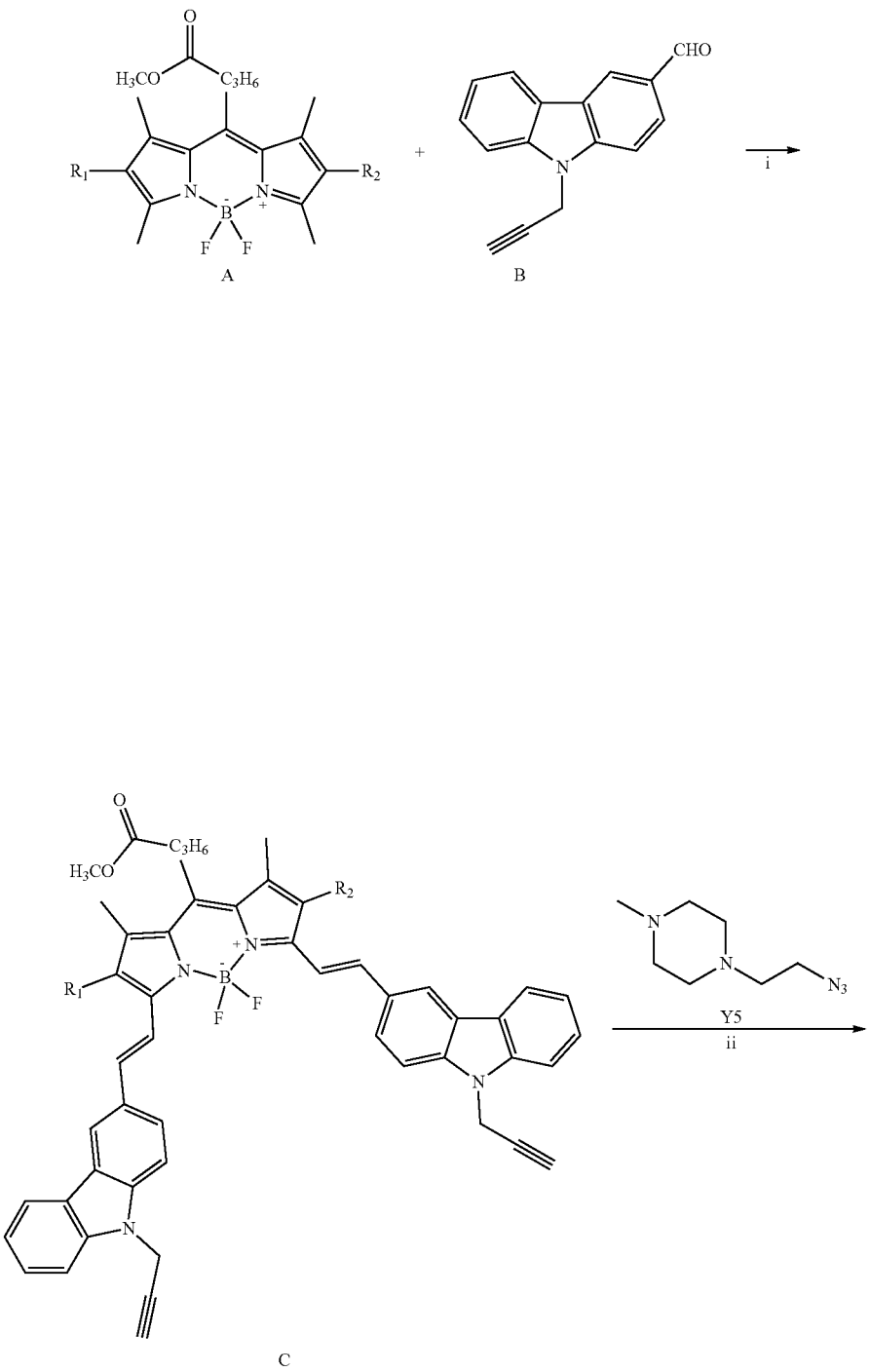

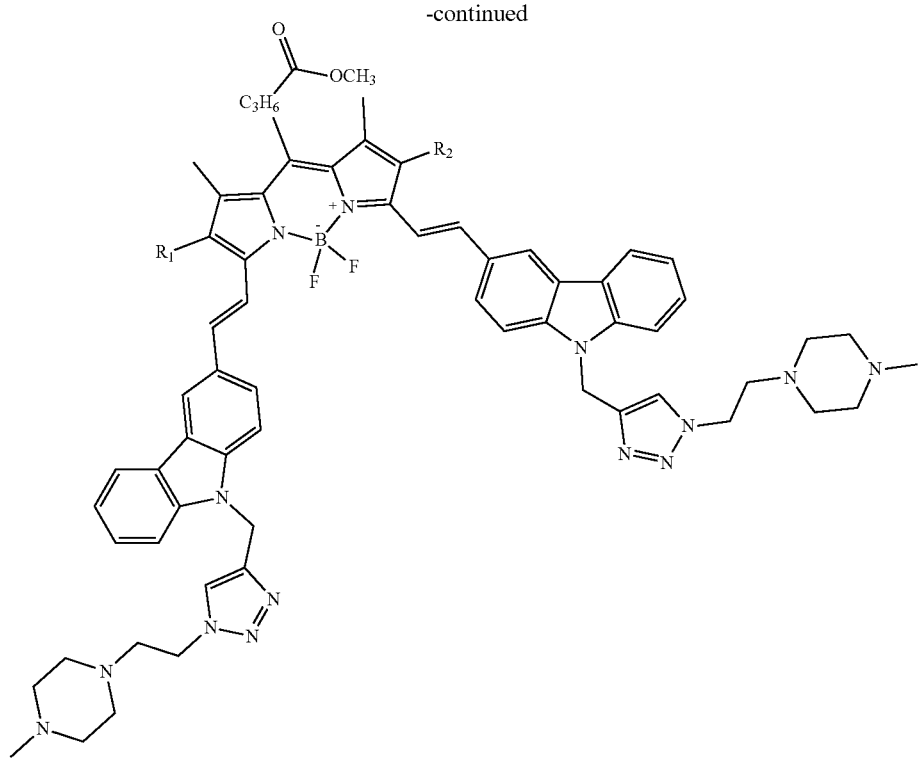
D
D42 R$_1$ = R$_2$ = Cl
D43 R$_1$ = R$_2$ = Br
D44 R$_1$ = R$_2$ = I
The synthesis method of compounds D42, D43 and D44 was the same as example 21.
Example 23
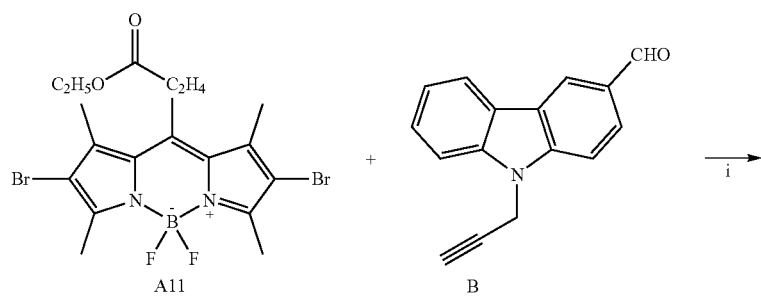

-continued

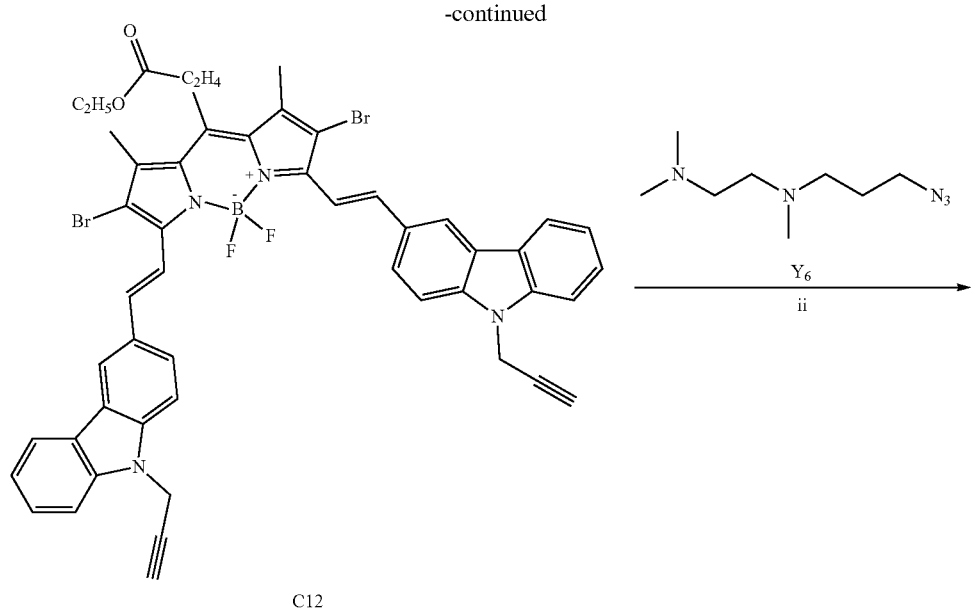
C12

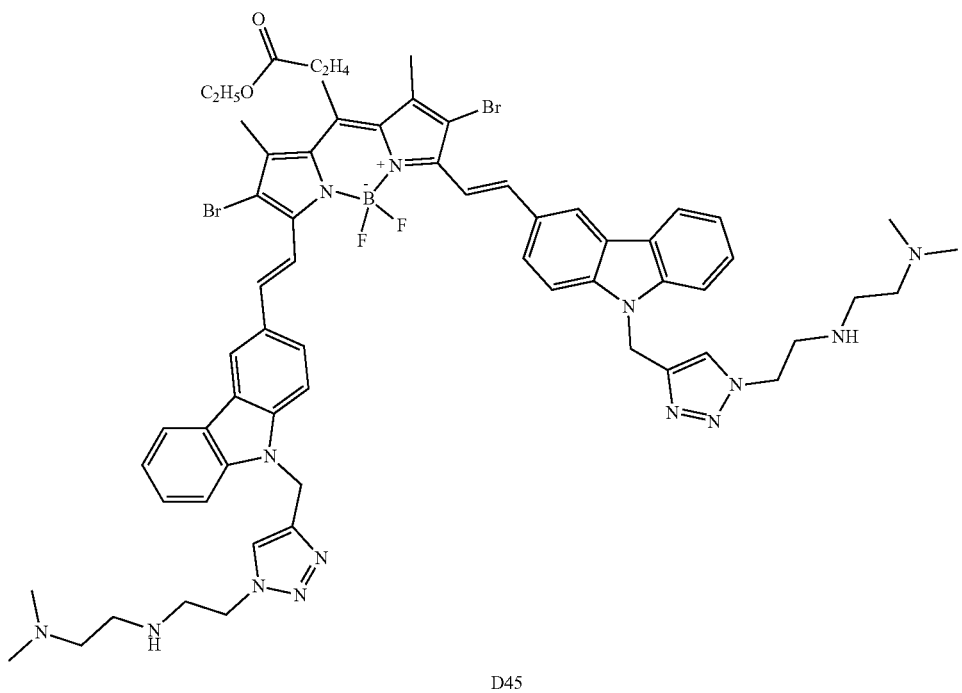
D45 i) A11 (1.27 mmol) and B (3.81 mmol) were added into 30 ml dry toluene (remove water with molecular sieve before use), then piperidine (1 ml) and glacial acetic acid (1 ml) were added to, then the reaction mixture was stirred at 150° C., while the water produced during the reaction was removed by water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chromatography ($CH_2Cl_2$/Petroleum ether, 1/3) to obtain compound C12.

ii) Under argon protection, compound C12 (66 μmol), Y6 (198 μmol), $CuSO_4.H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C12 was consumed completely. The resulting mixture was concentrated and purified by column chromatography to obtain compound D45.

Example 24
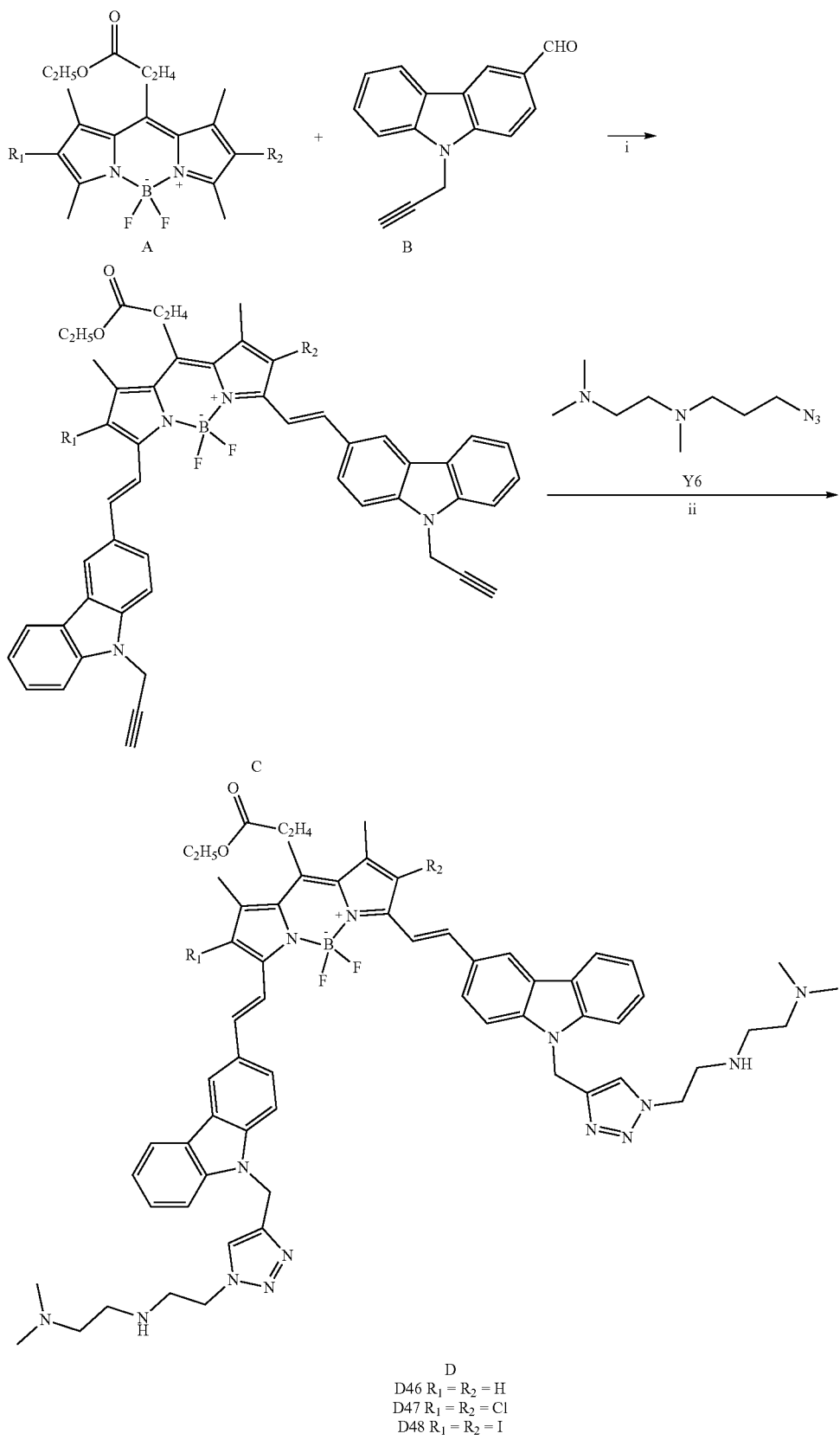
D
D46 R₁ = R₂ = H
D47 R₁ = R₂ = Cl
D48 R₁ = R₂ = I

The synthesis method of compounds D46, D47 and D48 was the same as example 23.
Example 25
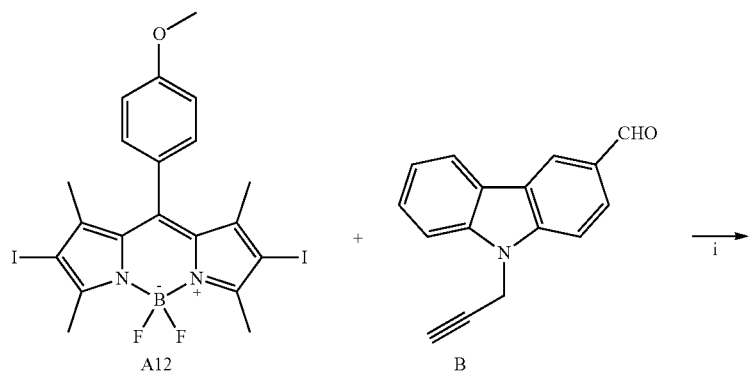
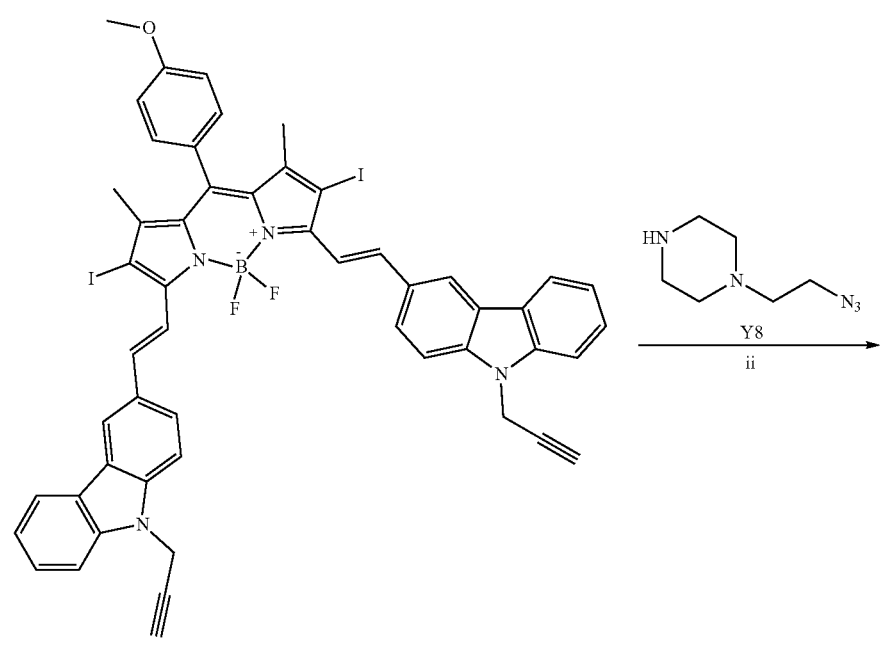

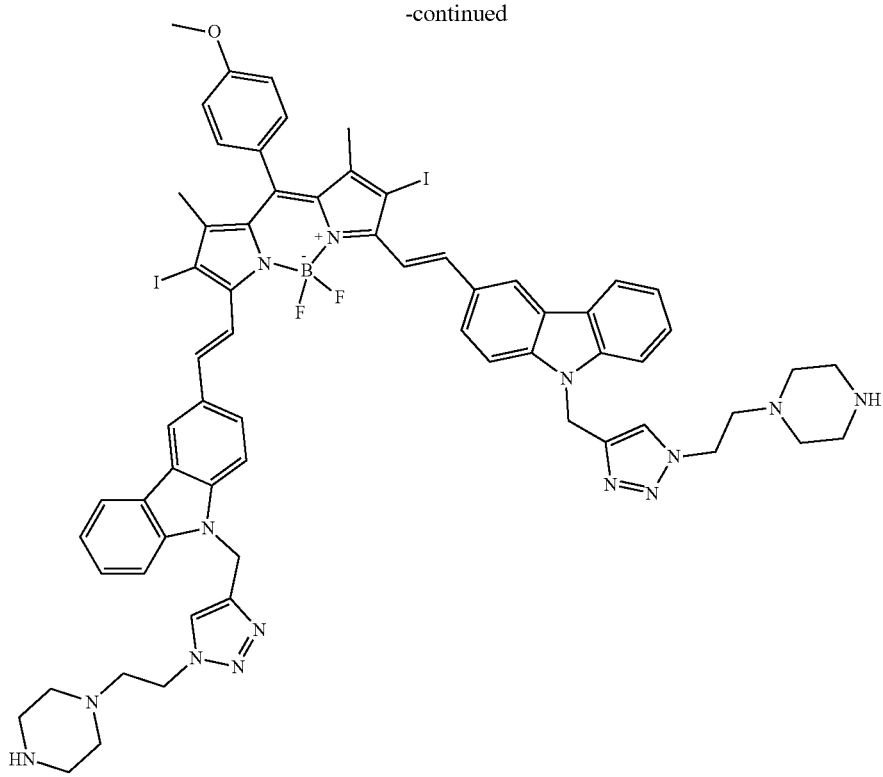

D49 i) A12 (1.27 mmol) and B (3.81 mmol) were added into 30 ml dry toluene (remove water with molecular sieve before use), then piperidine (1 ml) and glacial acetic acid (1 ml) were added to, then the reaction mixture was stirred at 150° C., while the water produced during the reaction was removed by water separator. The reaction was monitored by TLC until the end of the reaction. After cooling to room temperature, most of the toluene in the reaction mixture was evaporated under vacuum, and the remaining mixture was diluted with dichloromethane, washed with water, and concentrated. The crude product was purified by column chro[matography ($CH_2Cl_2$/Petroleum ether, 1/3) to obtain compound C13.

ii) Under argon protection, compound C13 (66 μmol), Y8 (198 μmol), $CuSO_4.H_2O$ (66 μmol) and Na ascorbate (132 μmol) were added into the mixture solution consisting of toluene, ethanol, and water (v/v/v=12/4/1), the mixture was stirred at room temperature monitoring by TLC until compound C13 was consumed completely. The resulting mixture was concentrated and purified by column chromatography to obtain compound D49.

Example 26

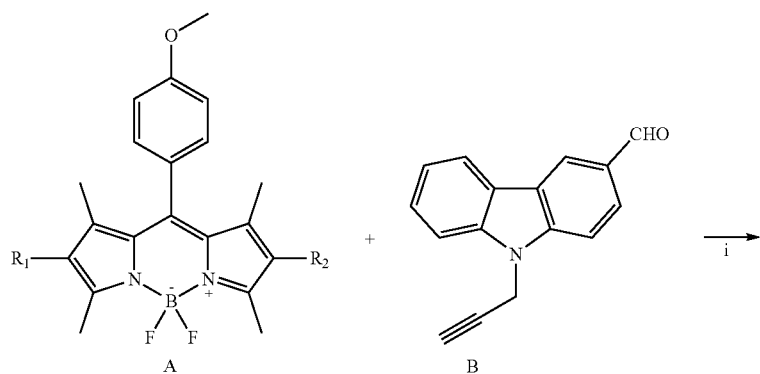

-continued

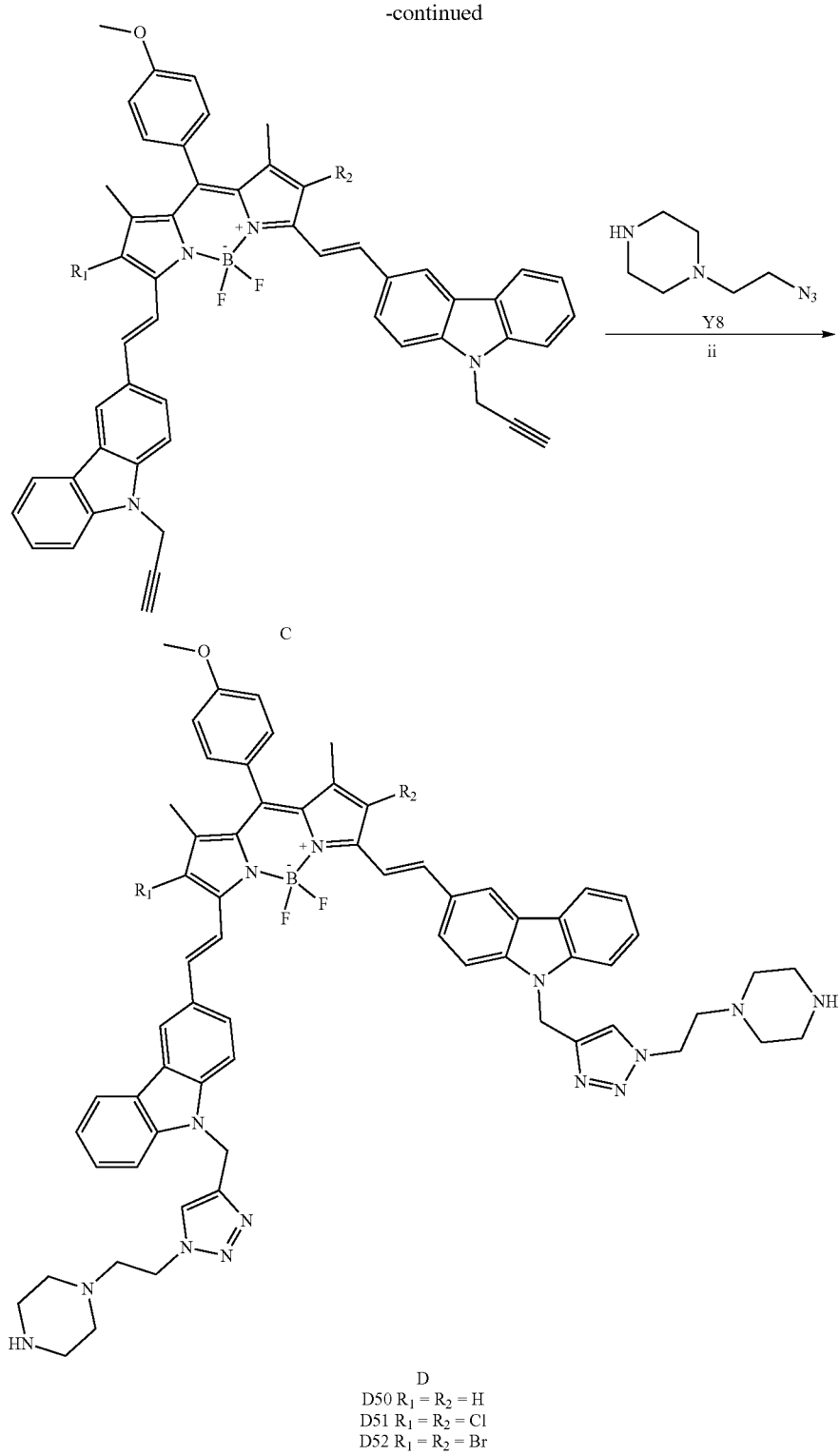

D
D50 R₁ = R₂ = H
D51 R₁ = R₂ = Cl
D52 R₁ = R₂ = Br

The synthesis method of compounds D50, D51 and D52 was the same as example 25.

Example 27

The photophysical properties of compounds D1, D2, D25 and D26 were investigated. Compounds D1, D2, D25 and D26 were dissolved in DMSO to obtain a 1 mM stock solution. The stock solution was further diluted with acetonitrile to obtain a 1 μM testing solution, of which 1 μL trifluoroacetic acid (0.1% by volume) was added. The absorption spectrum, emission spectrum, quantum yield and molar extinction coefficient of these testing solutions were measured. The absorption spectrum was recorded on Agilent 8453 UV-Vis-Spectrophotometer, and the fluorescent spectrum was recorded on an Agilent fluorescence spectrometer. The maximum absorption spectrum ($\lambda_{ab}$), the maximum emission spectrum ($\lambda_{em}$), the molar extinction coefficient ($\varepsilon$), and the fluorescence quantum yield ($\Phi^1$) of compounds D1, D2, D25 and D26 were shown in Table 1. As shown in Table 1, the maximum emission of compounds D1, D2, D25 and D26 were ranging from 600 nm to 750 nm, and those compounds have higher molar extinction coefficient and fluorescence quantum yield.

TABLE 1

Photophysical Properties of D1, D2, D25 and D26 in Acetonitrile.

| compound | solvent | $\lambda_{ab}/\lambda_{em}$ (nm) | $\varepsilon$ (M$^{-1}\cdot$cm$^{-1}$) × 10$^4$ | $\Phi^1$ |
|---|---|---|---|---|
| D1 | acetonitrile | 581/603 | 7.5 | 0.83 |
| D2 | acetonitrile | 604/650 | 10.4 | 0.63 |
| D25 | acetonitrile | 664/684 | 9.2 | 0.94 |
| D26 | acetonitrile | 692/732 | 11.3 | 0.72 |

Example 28

The properties of compounds D1, D2, D25 and D26 were investigated. Compounds D1, D2, D25 and D26 were dissolved in DMSO to obtain a 1 mM stock solution. The stock solution was further diluted with 2 mM CTAB (pH 3) or H$_2$O (pH 7) to obtain a 1 μM testing solution. The absorption spectrum and emission spectrum of the testing solution were measured. The evaluated method of photophysical properties was the same as example 13.

As shown in FIG. 1, a, b, c and d respectively are the emission spectrum of D1, D2, D25 and D26 in CTAB at pH 3 and H$_2$O (pH 7). CTAB (Hexadecyl trimethyl ammonium bromide) is a cationic surfactant with a critical micelle concentration of 0.9 mM. CTBA exists in the form of micelles in a 2 mM solution of CTAB, which not only helps dissolve dye molecules but also simulates the acidic microenvironment of lysosomes. As shown in the Figure, in 2 mM CTAB at pH 3, all four compounds in the lysosome-like microenvironment exhibited stable emission, while they showed almost no fluorescence in water at pH 7. It can be seen that four compounds showed no fluorescence outside cells, but stable and strong fluorescence in lysosomes. It is preliminarily determined that such property is in favor of confocal imaging of lysosomes without PBS washing.

Example 29

The photophysical properties of compounds D6, D15, D20, D22, D46 and D51 are provided in Table 2, following a similar testing method as example 14 and example 15. As shown in Table 2, the maximum emission wavelengths of compounds D6, D15, D20, D22, D46 and D51 are ranging from 600 nm to 750 nm, and also have higher molar extinction coefficient and fluorescent quantum yield. In 2 mM CTAB at pH 3, all six compounds in the lysosome-like microenvironment exhibited stable emission, but showed no fluorescence in water at pH 7. It can be seen that such property is in favor of confocal imaging of lysosomes without PBS washing.

TABLE 2

The photophysical properties of D6, D15, D20, D22, D46 and D51.

| | The photophysical properties in acetonitrile | | | In 2 mM CTAB at pH 3 | In water at pH 7 |
|---|---|---|---|---|---|
| Compound | $\lambda_{ab}/\lambda_{em}$ (nm) | $\varepsilon$ (M$^{-1}\cdot$cm$^{-1}$) × 10$^4$ | $\Phi^1$ | Fluorescence emission | Fluorescence emission |
| D6 | 590/615 | 8.1 | 0.73 | Stable fluorescent emission | No fluorescence |
| D15 | 615/665 | 9.9 | 0.78 | Stable fluorescent emission | No fluorescence |
| D20 | 609/655 | 10.1 | 0.84 | Stable fluorescent emission | No fluorescence |
| D22 | 611/661 | 10.8 | 0.81 | Stable fluorescent emission | No fluorescence |
| D46 | 659/675 | 11.0 | 0.89 | Stable fluorescent emission | No fluorescence |
| D51 | 689/728 | 11.1 | 0.79 | Stable fluorescent emission | No fluorescence |

Example 30

The fluorescent imaging of compounds D1, D6, D22 and D25. After incubating for 24 hours in a cell incubator with 5% CO$_2$ at 37° C., RAW 264.7 cells were incubated with 1 μM D1 or 1 μM D6 for 5 min, or incubated with 1 μM D22 or 1 μM D25 for 60 min, then incubated with 1 μM DND-26 which is green lysosome probe for 5 min, washed three times with PBS, then imaged using a confocal microscope.

Figure 2:
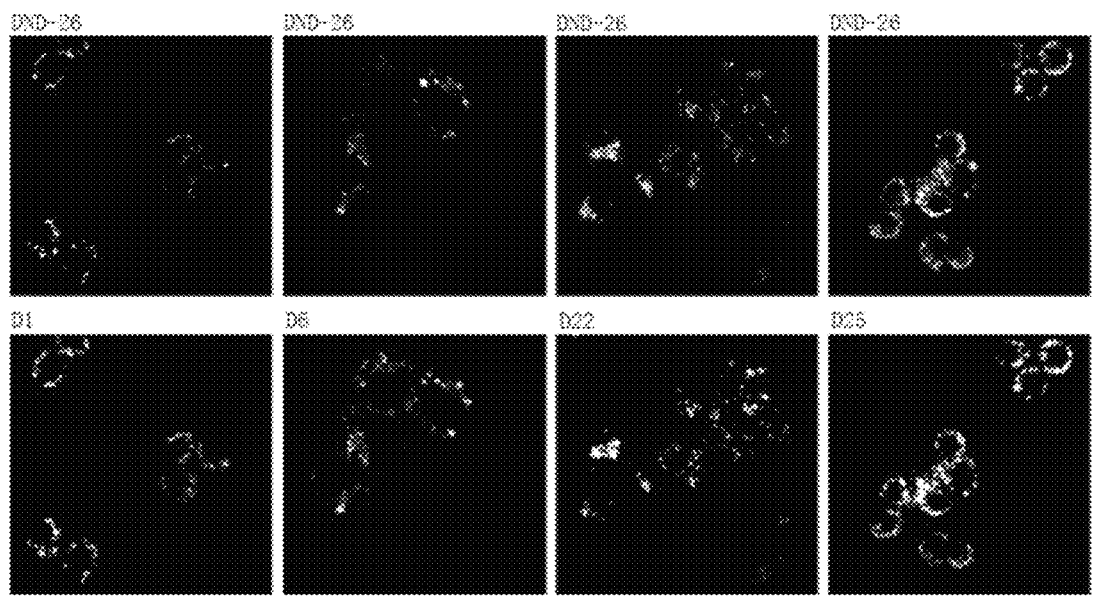
FIG. 2 is the image of live cell lysosomes co-stain with compounds D1, D6, D22 and D25.

As shown in FIG. 2, the first row is confocal images of DND-26, and the second row from left to right are confocal images of D1, D6, D22 and D25. It can be clearly observed from the confocal images that compound D1, D6, D22 and D25 can specifically target lysosomes.

Example 31

The fluorescence image of compounds D15, D20, D46 and D51. After incubating for 24 hours in a cell incubator with 5% CO$_2$ at 37° C., RAW 264.7 cells were incubated with 1 μM D15 or 1 μM D20 for 5 min, or incubated with 1 μM D46 or 1 μM D51 for 60 min, then incubated with 1 μM DND-26 for 5 min, washed three times with PBS, and then imaged using a confocal microscope.

Figure 3:
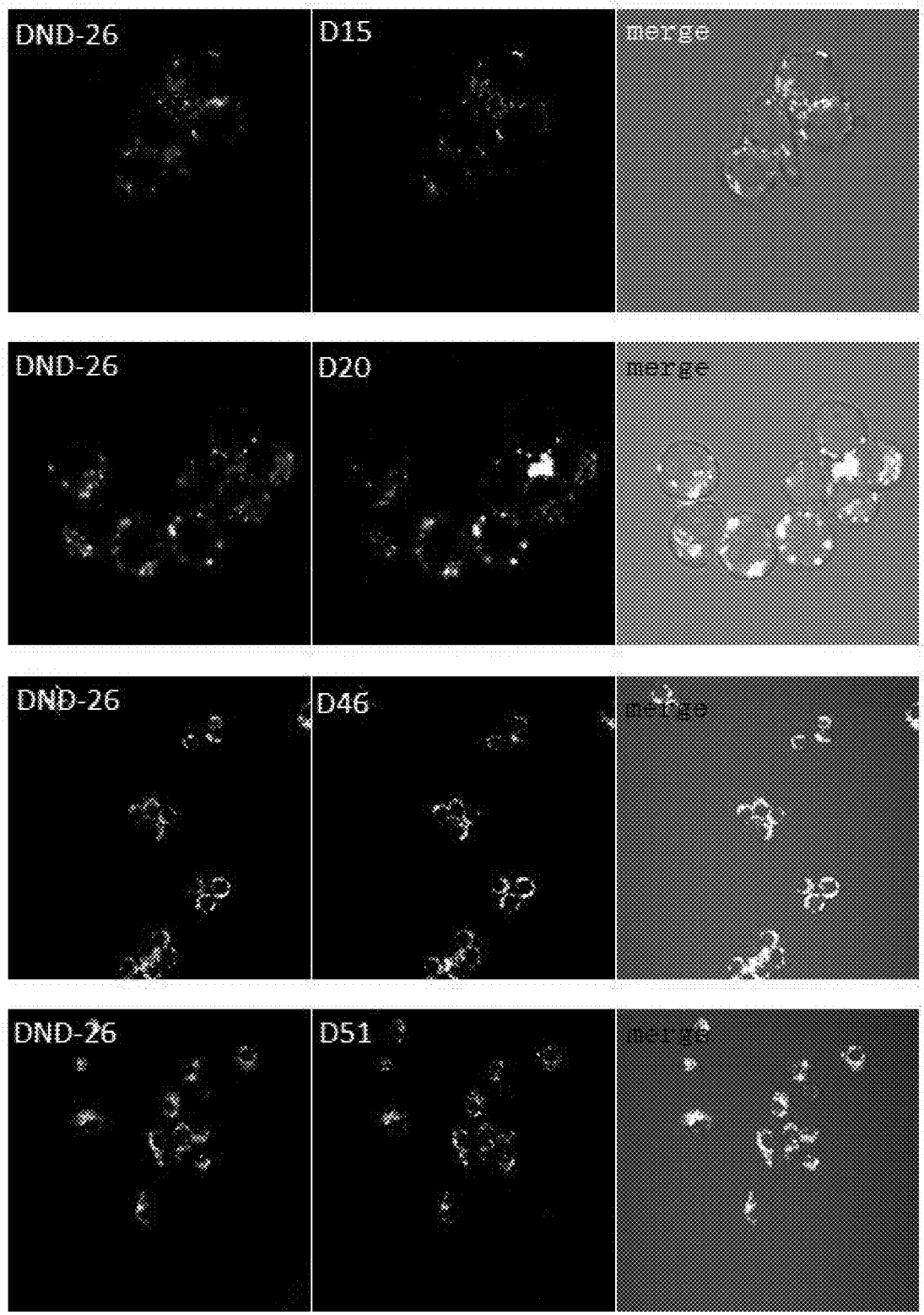
FIG. 3 is the image of live cell lysosomes co-stain with compounds D15, D20, D46 and D51.

FIG. 3 is the cell imaging co-localization figure of compounds D15, D20, D46, and D51. As shown in FIG. 3, it can be clearly observed from confocal images that compound D15, D20, D46 and D51 can specifically target lysosomes.

Example 32

Figure 4:
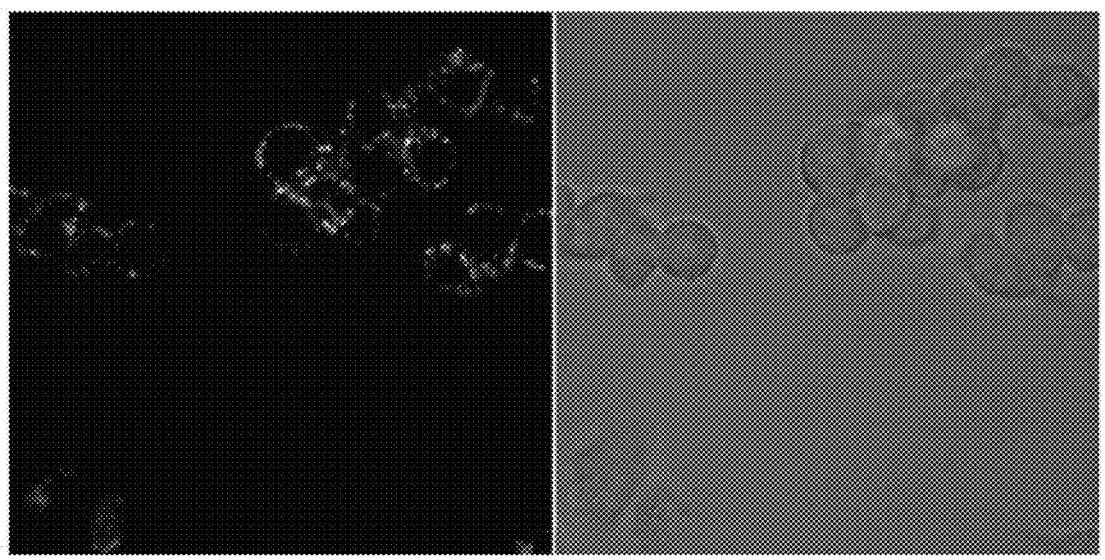
FIG. 4 is the image of live cell lysosomes with D25 without washing.

The fluorescence image of compound D25. After incubating for 24 hours in a cell incubator with 5% CO$_2$ at 37° C., RAW 264.7 cells were incubated with 100 nM D25 for 60 min and then imaged using a confocal microscope. As shown in FIG. 4, it can be clearly observed by confocal images that compound D25 can be used for lysosome images without washing.

Example 33

The fluorescence imaging of compound D25. After incubating for 24 hours in a cell incubator with 5% CO$_2$ at 37°

C., RAW 264.7 cells were incubated with 1 μM D25 for 60 min, then incubated with 1 μM DND-26 for 5 min, washed three times with PBS, and then imaged using a confocal microscope after adding 20 M chloroquine. Chloroquine can cause protons to escape from lysosomes, so it can be used to raise the pH of the lysosomes.

Figure 5:
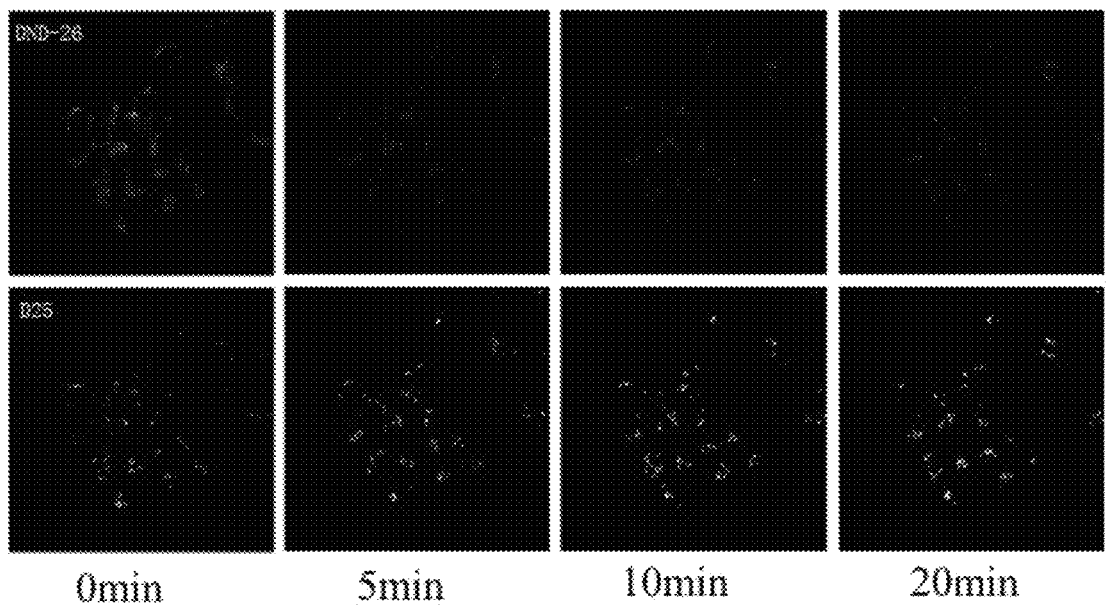
FIG. 5 is the image of live cell lysosomes with D25 stimulated with chloroquine.

As shown in FIG. 5, under the condition of co-staining with DND-26, after adding chloroquine, the fluorescence intensity of DND-26 decreased significantly within 5 min, while the fluorescence intensity of compound D25 only changed slightly. It can be seen that compound D25 shows stable fluorescence intensity which is independent of pH changes of lysosomes and can correctly indicate the location and morphology of lysosomes.

Example 34

We further investigate the targeting feature by imaging vesicles stained with D25 at pH 4.0 and pH 7.4.

The "droplet transfer" method was used to prepare vesicles composed of PC/Chol molar ratios of 7:3, following six steps as below: 1) Prepare 200 mM glucose aqueous solution and sucrose aqueous solution respectively. 2) Hydrophobic phase (0.3 mM PC in decane+0.3 mM CL in decane for PC/CL). 3) The hydrophobic phase was prepared by adding PC (0.3 mM) and possibly other lipids (SM and/or Chol) in decane. 4) Pipette the aqueous phase consisting of 20 μL of sucrose solution and the hydrophobic phase consisting of 600 μL PC/CL into a 1.5 ml centrifuge tube and shake them well. 5) Centrifuge the tube, then remove the mineral oil and wash the GUVs to remove excess solutes. 6) Suspend 30 μL of the pellet in 20 μL of 200 mM glucose solution. 7) Pipette 20 μL onto a glass slide and observe with a confocal microscope and fluorescence lifetime microscope.

Method for vesicles imaging, 30 μL of the vesicles was diluted with 20 μL of 200 mM glucose solution, then stained with D25 in pH 4 PBS (or in pH 7.4 PBS) for 60 min and imaged with a confocal microscope.

Figure 6:
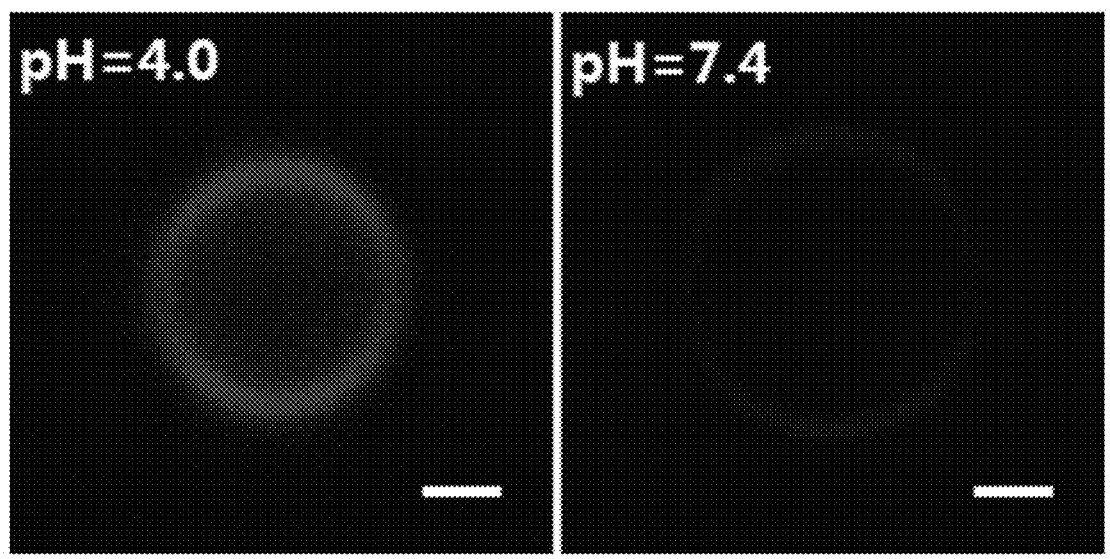
FIG. 6 is confocal image of vesicle stained with D25 at pH 4.0 and pH 7.4.

As shown in FIG. 6, the confocal image of vesicles stained by D25 showed intense fluorescence at pH 4, which demonstrates its ability to target membrane structure due to acidic-dependent amphiphilic structure. By contrast, the confocal image of vesicles stained by D25 showed weak fluorescence at pH 7.4, which demonstrates that D25 was not efficiently enriched in the membrane structure of vesicles at pH 7.4.

Example 35

We used D25 as a representative to evaluate its ability to perform STED-based super-resolution imaging. After incubating for 24 hours in a cell incubator with 5% $CO_2$ at 37° C., RAW 264.7 cells were stained with 250 nM D25 for 60 min and imaged using STED based microscope after replacing the staining solution with fresh MEM.

Figure 7:
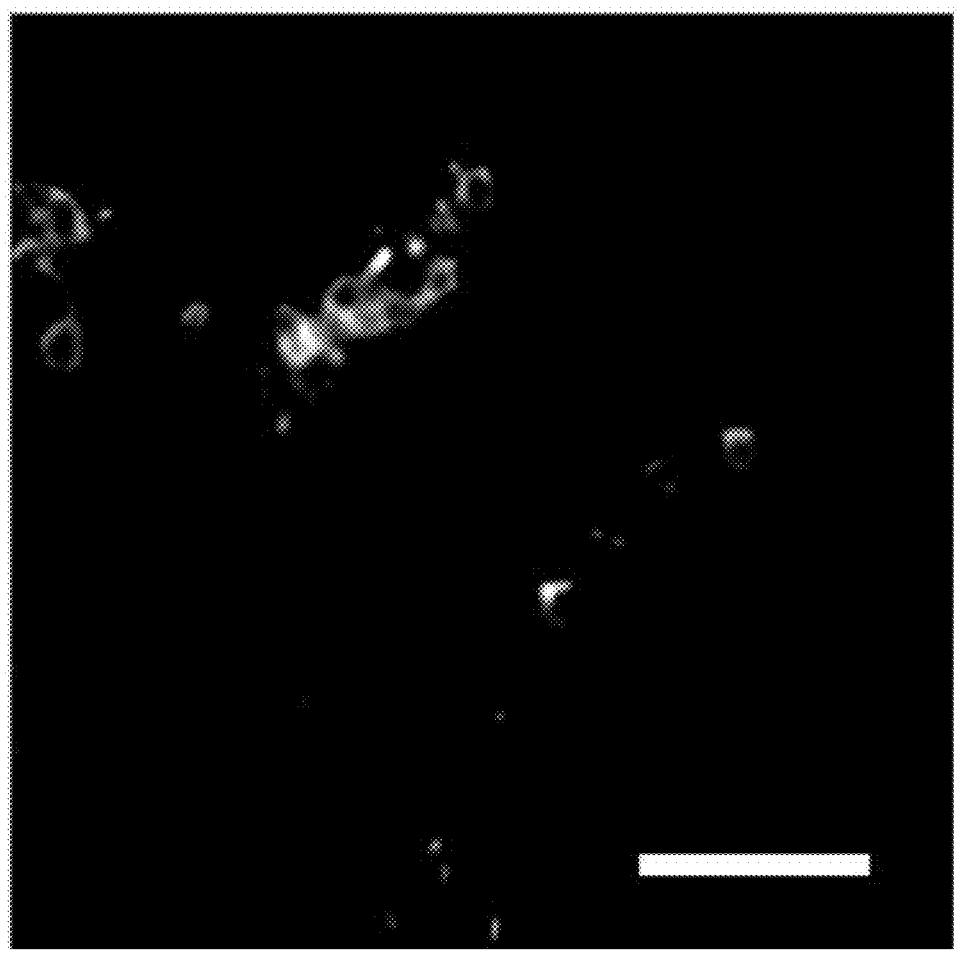
FIG. 7 is the super-resolution image of RAW 264.7 cells stained with D25.

As shown in FIG. 7, the super-resolution image of cells stained with D25 draws the shape of the lysosomal membrane clearly. This result is direct proof that D25 is indeed localized in the lysosomal membrane.

What is claimed is:

1. A compound of formula I:

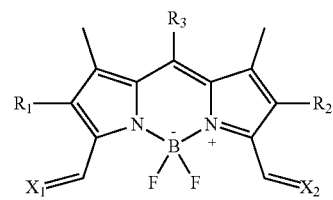

Wherein, $R_1$ and $R_2$ are each independently H, Cl, Br or I;

$R_3$ is H, $CH_3$, $CF_3$, $C_3H_6COOCH_3$, $C_2H_4COOC_2H_5$, $C_2H_5$,

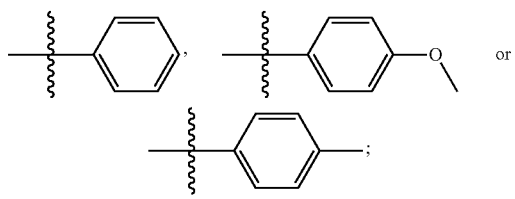

$X_1$ is

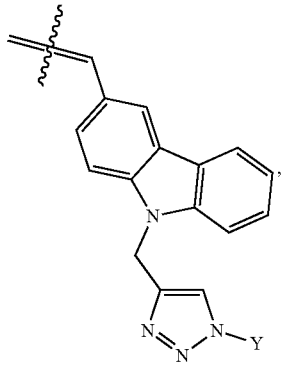

$X_2$ is H or

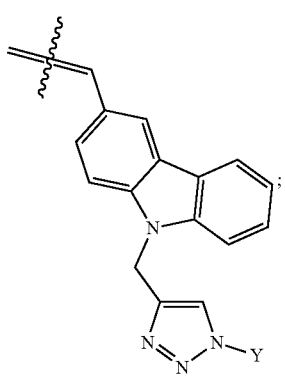

Y is each independently
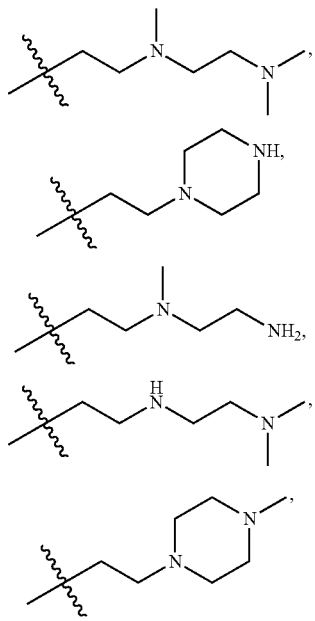
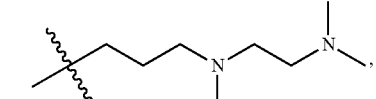
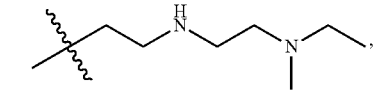
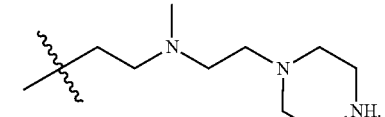
2. A composition targeting or tracking lysosomes comprising a compound of claim 1.
3. A composition comprising a compound of claim 1 in a solvent, wherein the solvent is selected from the group consisting of water, dimethylformamide, dimethyl acetamide, dimethyl sulfoxide, nitrogen methyl pyrrolidone, and acetonitrile.
* * * * *